(12) United States Patent (10) Patent No.: US 7,989,090 B2
Thompson et al. (45) Date of Patent: Aug. 2, 2011

(54) NEAR INFRARED EMITTING ORGANIC COMPOUNDS AND ORGANIC DEVICES USING THE SAME

(75) Inventors: Mark E. Thompson, Anaheim, CA (US); Carsten Borek, Pasadena, CA (US); Kenneth Hanson, Los Angeles, CA (US); Peter Djurovich, Long Beach, CA (US); Yiru Sun, Princeton, NJ (US); Stephen Forrest, Ann Arbor, MI (US); Arnold Tamayo, Glendale, CA (US)

(73) Assignees: The Trustees of Princeton University, Princeton, NJ (US); The University of Southern California, Los Angeles, CA (US); The Regents of the University of Michigan, Ann Arbor, MI (US)

( * ) Notice: Subject to any disclaimer, the term of this patent is extended or adjusted under 35 U.S.C. 154(b) by 0 days.

(21) Appl. No.: 12/546,829

(22) Filed: Aug. 25, 2009

(65) Prior Publication Data

US 2010/0013386 A1 Jan. 21, 2010

Related U.S. Application Data

(62) Division of application No. 11/518,311, filed on Sep. 11, 2006, now Pat. No. 7,598,381.

(51) Int. Cl.
*H05B 33/14* (2006.01)
*H05B 33/00* (2006.01)
(52) U.S. Cl. ........................................ 428/690; 313/504
(58) Field of Classification Search .................. 428/690; 313/504
See application file for complete search history.

(56) References Cited

U.S. PATENT DOCUMENTS

| | | | |
|---|---|---|---|
| 4,769,292 A | 9/1988 | Tang et al. | |
| 5,703,436 A | 12/1997 | Forrest et al. | |
| 5,707,745 A | 1/1998 | Forrest et al. | |
| 5,718,842 A | 2/1998 | Papkovsky et al. | |
| 5,834,893 A | 11/1998 | Bulovic et al. | |
| 5,844,363 A | 12/1998 | Gu et al. | |
| 6,013,982 A | 1/2000 | Thompson et al. | |
| 6,087,196 A | 7/2000 | Sturm et al. | |
| 6,091,195 A | 7/2000 | Forrest et al. | |
| 6,097,147 A | 8/2000 | Baldo et al. | |
| 6,294,398 B1 | 9/2001 | Kim et al. | |
| 6,303,238 B1 | 10/2001 | Thompson et al. | |
| 6,310,360 B1 | 10/2001 | Forrest et al. | |
| 6,337,102 B1 | 1/2002 | Forrest et al. | |
| 6,395,555 B1 * | 5/2002 | Wilson et al. | 436/68 |
| 6,468,819 B1 | 10/2002 | Kim et al. | |
| 6,548,956 B2 | 4/2003 | Forrest et al. | |
| 6,576,134 B1 | 6/2003 | Agner | |
| 6,602,540 B2 | 8/2003 | Gu et al. | |
| 6,908,695 B2 * | 6/2005 | Seo et al. | 428/690 |
| 7,071,615 B2 | 7/2006 | Lu et al. | |
| 2002/0034656 A1 | 3/2002 | Thompson et al. | |
| 2002/0182441 A1 | 12/2002 | Lamansky et al. | |
| 2003/0034722 A1 | 2/2003 | Tsuboyama et al. | |
| 2003/0059647 A1 | 3/2003 | Thompson et al. | |
| 2003/0072964 A1 | 4/2003 | Kwong et al. | |
| 2003/0186077 A1 | 10/2003 | Chen | |
| 2003/0226996 A1 | 12/2003 | Aramaki et al. | |
| 2003/0230980 A1 | 12/2003 | Forrest et al. | |
| 2005/0170209 A1 | 8/2005 | Lee et al. | |

FOREIGN PATENT DOCUMENTS

| | | |
|---|---|---|
| JP | 61 206259 | 9/1986 |
| JP | 06 222409 | 8/1994 |
| JP | 2004/314327 | 11/2004 |
| WO | WO 02/15645 | 2/2002 |
| WO | WO 02/074015 | 9/2002 |
| WO | WO 02/094910 | 11/2002 |

OTHER PUBLICATIONS

U.S. Appl. No. 10/233,470, filed Sep. 4, 2002, Shtein et al.
PCT International Search Report and Written Opinion from PCT/US2007/016289, mailed on Oct. 30, 2008.
Adachi et al., "Nearly 100% Internal Phosphorescent Efficiency in an Organic Light Emitting Device," J. Appl. Phys. 90:5048, 2001.
Baldo et al., "Highly Efficient Phosphorescent Emission from Organic Electroluminescent Devices", Nature 395:151-154, 1998.
Baldo et al., "Very high efficiency green organic light-emitting devices based on electrophosphorescence," Appl. Phys.Lett. 75(3):4-6, 1999.
Brooks et al., Synthesis and characterization of phosphorescent cyclometalated platinum complexes, Inorg Chem. Jun. 17, 2002; 41(12):3055-66.
Burghart et al., 3,5-Diaryl-4,4-difluoro-4-bora-3a,4a-diaza-s-indacene (BODIPY) Dyes: Synthesis, Spectroscopic, Electrochemical and Structural Properties, J. Org. chem., 64:7813-7819, 1999.
Chen et al., "Room-temperature NIR phosphorescence of new iridium (III) Complexes with ligands derived frombenzoquinoxaline", Can. J. Chem., 84:309-318, 2006.
Cheng et al., "1.1 µm near-infrared electrophosphorescence from organic light-emitting diodes based on copper phtalocyanine", Appl. Phys. Lett. 88:213505-7,2006.
Finikova et al., "Novel Versatile Synthesis of Substituted Tetrabenzoporphyrins", J. Org. Chem., 69:522-536, 2004.
Finikova et al., "Synthesis and Luminescence of Soluble meso-Unsubstituted Tetrabenzo- and Tetranaphtho[2,3]porphyrins", J. Org. Chem., 70:9562-9572, 2005.
Finikova et al., "Synthesis of Symmetrical Tetraaryltetranaphtho[2,3]porphyrins" J. Org. Chem. 70:4617-4628, 2005.

(Continued)

*Primary Examiner* — Charanjit Aulakh
(74) *Attorney, Agent, or Firm* — Kenyon & Kenyon LLP

(57) ABSTRACT

Certain iridium compounds which may comprise an iridium (III)-ligand complex having the general formula: (C^N)$_2$—Ir—(N^N). (C^N) and (N^N) may each represent a ligand coordinated to an iridium atom. The iridium compounds may have a primary phosphorescent photoluminescence peak wavelength in the near-infrared (IR) range. Also, organic devices that use certain iridium compounds. The organic device may comprise an organic layer and the organic layer may comprise any of the iridium compounds disclosed herein. Also, organic devices that use certain metalloporphyrin compounds. The metalloporphyrin compounds may comprise a core porphyrin structure with four pyrrole rings. The metalloporphyrin compounds may have a primary phosphorescent photoluminescence peak wavelength in the near-IR range.

17 Claims, 11 Drawing Sheets

OTHER PUBLICATIONS

Gabe et al., "Highly sensitive fluorescence probes for nitric oxide based on boron dipyrromethene chromophore-rational design of potentially useful bioimaging fluorescence probe" J Am Chem Soc. Mar. 17, 2004;126(10):3357-67.

Flora et al., Guest Emission Processes in Dpoped Organic Light-Emitting Diodes: Use of Phthalocyanine and Naphthalocyanine Near-IR Dopants, J. Phys. Chem. 107:1142-50, 2003.

Harrison et al., "Near-Infrared electroluminescence from conjugated polymer/lanthanide porphyrin blends", Appl. Phys. Lett 79:3770-3772, 2001.

Krishnan et al., "Infrared applications for portable devices using IrDA transceivers", Optical Wireless Communications IV, 4530:104-115, 2000.

Lai et al., Electrogenerated Chemiluminescence 71. Photophysical, Electrochemical, and Electrogenerated Chemiluminescent Properties of Selected Dipyrromethene-$BF_2$ Dyes, J. Phys. Chem., 107:5036-5042, 2003.

Liddiard et al., "Future advances in uncooled IR sensor technology", Infrared Technology and Applications XXVI, 4130:119-127, 2000.

Ono et al., "A New Synthesis of Functional Dyes From 2-Acenaphtho[1,2-c]pyrrole", Heterocycles 61:433-447, 2003.

Lamansky et al., "Highly phosphorescent bis-cyclometalated iridium complexes: synthesis, photophysical characterization, and use in organic light emitting diodes", J Am Chem Soc. May 9, 2001;123(18):4304-12.

Ostrowski et al., "Near-Infrared Electroluminescent Light-Emitting Devices Based on Ethyne Bridged Porphyrin Fluorophores", Adv. Materials 15:1296-1300, 2003.

Ozawa et al., "Synthesis of end-functionalized $\pi$-conjugated porphyrin oligomers", Tetrahedron 62:4749-4755, 2006.

Porumb et al., "Infrared radiometer with digital signal processing for medical applications", ROMOPTO 2000, Sixth Conference on Optics, 4430:674-679, 2000.

Slooff and Polman, "Near-infrared electroluminescence of polymer light-emitting diodes doped with a lissamine-sensitized $Nd^{3+}$ complex", Appl. Phys. Lett., 78:21222124, 2001.

Wagner et al., "Boron-dipyrromethene dyes for incorporation in synthetic multi-pigment light-harvesting arrays", Pure and Appl. Chem. 68:1373-1380, 1996.

Xu et al.,"High power mid-infrared optically pumped PbSe/PbSrSe multiple-quantum-well vertical-cavity surface-emitting laser operation at 325K", Electronics Lett 39:659-661, 2003.

* cited by examiner

US 7,989,090 B2

NEAR INFRARED EMITTING ORGANIC COMPOUNDS AND ORGANIC DEVICES USING THE SAME

CROSS-REFERENCE TO RELATED APPLICATIONS

This application is a division of U.S. Ser. No. 11/518,311 filed Sep. 11, 2006, now U.S. Pat. No. 7,598,381 which is incorporated by reference in its entirety.

This invention was made with support from the United States Government, under Contract No. W15P7T-06-C-T201, awarded by the Army Research Office. The Government has certain rights in this invention.

The claimed invention was made by, on behalf of, and/or in connection with one or more of the following parties to a joint university corporation research agreement: Princeton University, The University of Southern California, and the Universal Display Corporation. The agreement was in effect on and before the date the claimed invention was made, and the claimed invention was made as a result of activities undertaken within the scope of the agreement.

FIELD OF THE INVENTION

The present invention relates to organic light emitting devices (OLEDs), and more specifically to organic materials used in such devices.

BACKGROUND

Opto-electronic devices that make use of organic materials are becoming increasingly desirable for a number of reasons. Many of the materials used to make such devices are relatively inexpensive, so organic opto-electronic devices have the potential for cost advantages over inorganic devices. In addition, the inherent properties of organic materials, such as their flexibility, may make them well suited for particular applications such as fabrication on a flexible substrate. Examples of organic opto-electronic devices include organic light emitting devices (OLEDs), organic phototransistors, organic photovoltaic cells, and organic photodetectors. For OLEDs, the organic materials may have performance advantages over conventional materials. For example, the wavelength at which an organic emissive layer emits light may generally be readily tuned with appropriate dopants.

As used herein, the term "organic" includes polymeric materials as well as small molecule organic materials that may be used to fabricate organic opto-electronic devices. "Small molecule" refers to any organic material that is not a polymer, and "small molecules" may actually be quite large. Small molecules may include repeat units in some circumstances. For example, using a long chain alkyl group as a substituent does not remove a molecule from the "small molecule" class. Small molecules may also be incorporated into polymers, for example as a pendent group on a polymer backbone or as a part of the backbone. Small molecules may also serve as the core moiety of a dendrimer, which consists of a series of chemical shells built on the core moiety. The core moiety of a dendrimer may be a fluorescent or phosphorescent small molecule emitter. A dendrimer may be a "small molecule," and it is believed that all dendrimers currently used in the field of OLEDs are small molecules. In general, a small molecule has a well-defined chemical formula with a single molecular weight, whereas a polymer has a chemical formula and a molecular weight that may vary from molecule to molecule. As used herein, "organic" includes metal complexes of hydrocarbyl and heteroatom-substituted hydrocarbyl ligands.

OLEDs make use of thin organic films that emit light when voltage is applied across the device. OLEDs are becoming an increasingly interesting technology for use in applications such as flat panel displays, illumination, and backlighting. Several OLED materials and configurations are described in U.S. Pat. Nos. 5,844,363, 6,303,238, and 5,707,745, which are incorporated herein by reference in their entirety.

OLED devices are generally (but not always) intended to emit light through at least one of the electrodes, and one or more transparent electrodes may be useful in an organic opto-electronic devices. For example, a transparent electrode material, such as indium tin oxide (ITO), may be used as the bottom electrode. A transparent top electrode, such as disclosed in U.S. Pat. Nos. 5,703,436 and 5,707,745, which are incorporated by reference in their entireties, may also be used. For a device intended to emit light only through the bottom electrode, the top electrode does not need to be transparent, and may be comprised of a thick and reflective metal layer having a high electrical conductivity. Similarly, for a device intended to emit light only through the top electrode, the bottom electrode may be opaque and/or reflective. Where an electrode does not need to be transparent, using a thicker layer may provide better conductivity, and using a reflective electrode may increase the amount of light emitted through the other electrode, by reflecting light back towards the transparent electrode. Fully transparent devices may also be fabricated, where both electrodes are transparent. Side emitting OLEDs may also be fabricated, and one or both electrodes may be opaque or reflective in such devices.

As used herein, "top" means furthest away from the substrate, while "bottom" means closest to the substrate. For example, for a device having two electrodes, the bottom electrode is the electrode closest to the substrate, and is generally the first electrode fabricated. The bottom electrode has two surfaces, a bottom surface closest to the substrate, and a top surface further away from the substrate. Where a first layer is described as "disposed over" a second layer, the first layer is disposed further away from substrate. There may be other layers between the first and second layer, unless it is specified that the first layer is "in physical contact with" the second layer. For example, a cathode may be described as "disposed over" an anode, even though there are various organic layers in between.

As used herein, "solution processible" means capable of being dissolved, dispersed, or transported in and/or deposited from a liquid medium, either in solution or suspension form.

As used herein, and as would be generally understood by one skilled in the art, a first "Highest Occupied Molecular Orbital" (HOMO) or "Lowest Unoccupied Molecular Orbital" (LUMO) energy level is "greater than" or "higher than" a second HOMO or LUMO energy level if the first energy level is closer to the vacuum energy level. Since ionization potentials (IP) are measured as a negative energy relative to a vacuum level, a higher HOMO energy level corresponds to an IP having a smaller absolute value (an IP that is less negative). Similarly, a higher LUMO energy level corresponds to an electron affinity (EA) having a smaller absolute value (an EA that is less negative). On a conventional energy level diagram, with the vacuum level at the top, the LUMO energy level of a material is higher than the HOMO energy level of the same material. A "higher" HOMO or LUMO energy level appears closer to the top of such a diagram than a "lower" HOMO or LUMO energy level.

SUMMARY OF THE INVENTION

In one aspect, the present invention provides an iridium compound having the formula:

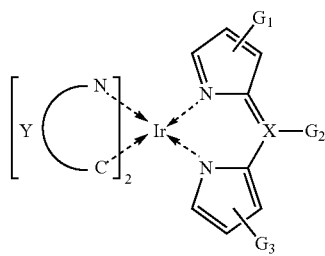

wherein $G_2$ is a hydrogen, phenyl, substituted phenyl, or alkyl;

wherein $G_1$ is a hydrogen, aryl moiety, or heteroaryl moiety on any position of the adjoining pyrrole ring;

wherein $G_3$ is a hydrogen, aryl moiety, or heteroaryl moiety on any position of the adjoining pyrrole ring;

wherein X is a nitrogen or carbon atom; and wherein the ligand

contains a phenylpyrazole moiety, phenylpyridine moiety, or phenyloxazol moiety.

In another aspect, the present invention provides an organic device comprising an iridium compound.

In another aspect, the present invention provides an organic device comprising a metalloporphyrin compound, wherein the compound comprises a plurality of pyrrole rings and has a formula:

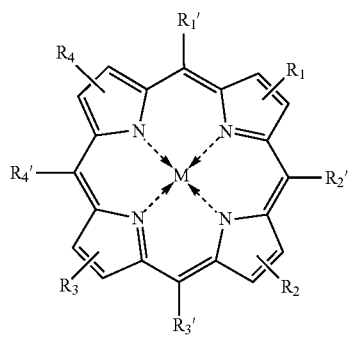

wherein M is a metal;

wherein each of $R_1$ to $R_4$ is independently selected from the group consisting of an aliphatic moiety, aryl moiety, heteroaryl moiety, and macrocycle moiety;

wherein each of $R_1'$ to $R_4'$ is independently selected from the group consisting of a hydrogen, phenyl, mesityl, and methyl; and wherein the compound has a primary phosphorescent photoluminescence emission peak wavelength in the near-infrared range.

DETAILED DESCRIPTION

Figure 1:
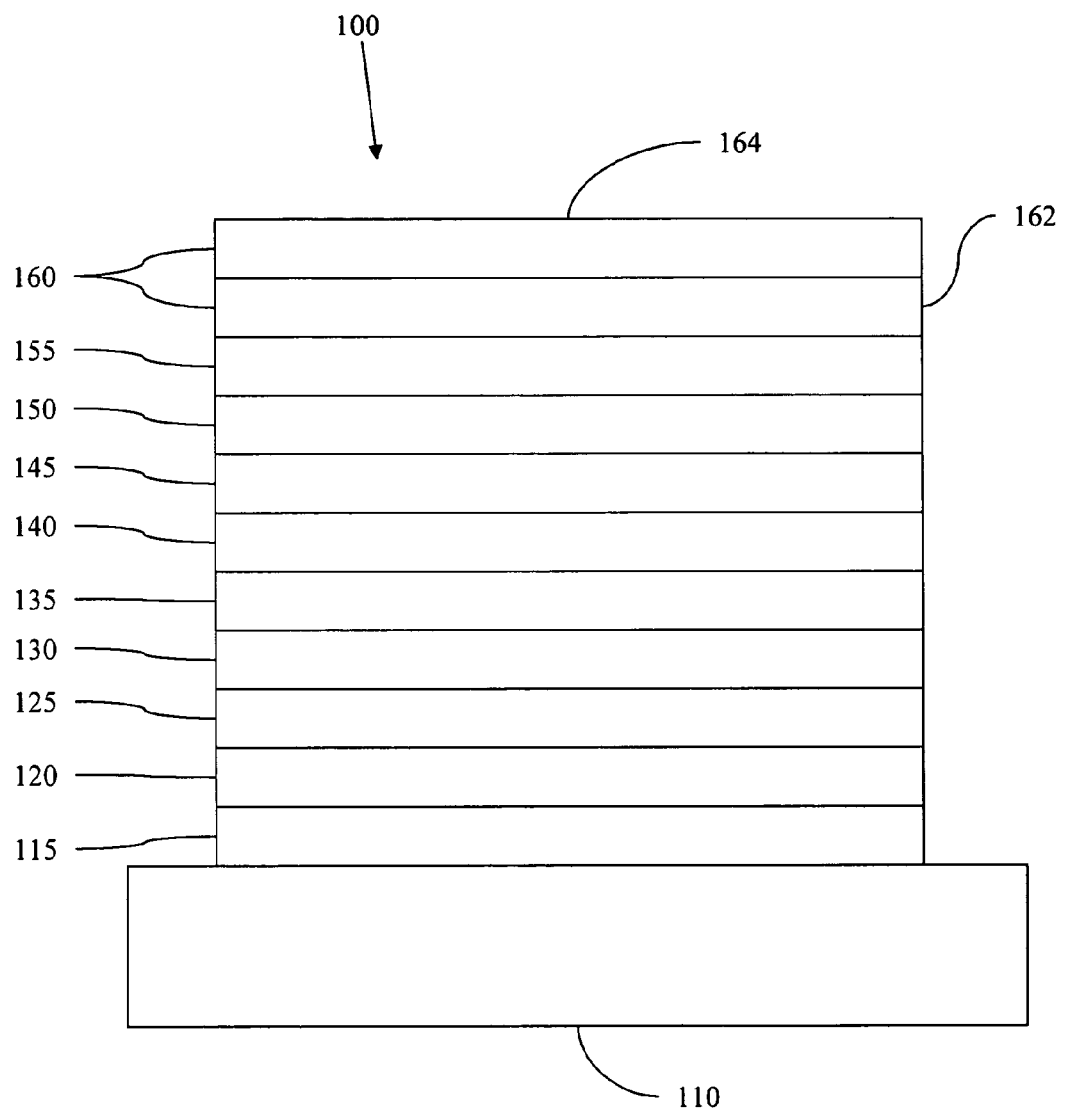
FIG. 1 shows an organic light emitting device having separate electron transport, hole transport, and emissive layers, as well as other layers.

Generally, an OLED comprises at least one organic layer disposed between and electrically connected to an anode and a cathode. When a current is applied, the anode injects holes and the cathode injects electrons into the organic layer(s). The injected holes and electrons each migrate toward the oppositely charged electrode. When an electron and hole localize on the same molecule, an "exciton," which is a localized electron-hole pair having an excited energy state, is formed. Light is emitted when the exciton relaxes via a photoemissive mechanism. In some cases, the exciton may be localized on an excimer or an exciplex. Non-radiative mechanisms, such as thermal relaxation, may also occur, but are generally considered undesirable.

The initial OLEDs used emissive molecules that emitted light from their singlet states ("fluorescence") as disclosed, for example, in U.S. Pat. No. 4,769,292, which is incorporated by reference in its entirety. Fluorescent emission generally occurs in a time frame of less than 10 nanoseconds.

More recently, OLEDs having emissive materials that emit light from triplet states ("phosphorescence") have been demonstrated. Baldo et al., "Highly Efficient Phosphorescent Emission from Organic Electroluminescent Devices," Nature, vol. 395, 151-154, 1998; ("Baldo-I") and Baldo et al., "Very high-efficiency green organic light-emitting devices based on electrophosphorescence," Appl. Phys. Lett., vol. 75, No. 1, 4-6 (1999) ("Baldo-II"), which are incorporated by reference in their entireties. Phosphorescence may be referred to as a "forbidden" transition because the transition requires a change in spin states, and quantum mechanics indicates that such a transition is not favored. As a result, phosphorescence generally occurs in a time frame exceeding at least 10 nanoseconds, and typically greater than 100 nanoseconds. If the natural radiative lifetime of phosphorescence is too long, triplets may decay by a non-radiative mechanism, such that no light is emitted. Organic phosphorescence is also often observed in molecules containing heteroatoms with unshared pairs of electrons at very low temperatures. 2,2'-bipyridine is such a molecule. Non-radiative decay mechanisms are typically temperature dependent, such that an organic material that exhibits phosphorescence at liquid nitrogen temperatures typically does not exhibit phosphorescence at room temperature. But, as demonstrated by Baldo, this problem may be addressed by selecting phosphorescent compounds that do phosphoresce at room temperature. Representative emissive layers include doped or un-doped phosphorescent organometallic materials such as disclosed in U.S. Pat. Nos. 6,303,238 and 6,310,360; U.S. Patent Application Publication Nos. 2002-0034656; 2002-0182441; 2003-0072964; and WO-02/074015.

Generally, the excitons in an OLED are believed to be created in a ratio of about 3:1, i.e., approximately 75% triplets and 25% singlets. See, Adachi et al., "Nearly 100% Internal Phosphorescent Efficiency In An Organic Light Emitting Device," J. Appl. Phys., 90, 5048 (2001), which is incorporated by reference in its entirety. In many cases, singlet excitons may readily transfer their energy to triplet excited states via "intersystem crossing," whereas triplet excitons may not readily transfer their energy to singlet excited states. As a result, 100% internal quantum efficiency is theoretically possible with phosphorescent OLEDs. In a fluorescent device, the energy of triplet excitons is generally lost to radiationless decay processes that heat-up the device, resulting in much lower internal quantum efficiencies. OLEDs utilizing phosphorescent materials that emit from triplet excited states are disclosed, for example, in U.S. Pat. No. 6,303,238, which is incorporated by reference in its entirety.

Phosphorescence may be preceded by a transition from a triplet excited state to an intermediate non-triplet state from which the emissive decay occurs. For example, organic molecules coordinated to lanthanide elements often phosphoresce from excited states localized on the lanthanide metal. However, such materials do not phosphoresce directly from a triplet excited state but instead emit from an atomic excited state centered on the lanthanide metal ion. The europium diketonate complexes illustrate one group of these types of species.

Phosphorescence from triplets can be enhanced over fluorescence by confining, preferably through bonding, the organic molecule in close proximity to an atom of high atomic number. This phenomenon, called the heavy atom effect, is created by a mechanism known as spin-orbit coupling. Such a phosphorescent transition may be observed from an excited metal-to-ligand charge transfer (MLCT) state of an organometallic molecule such as tris(2-phenylpyridine)iridium(III).

As used herein, the term "triplet energy" refers to an energy corresponding to the highest energy feature discernable in the phosphorescence spectrum of a given material. The highest energy feature is not necessarily the peak having the greatest intensity in the phosphorescence spectrum, and could, for example, be a local maximum of a clear shoulder on the high energy side of such a peak.

FIG. 1 shows an organic light emitting device 100. The figures are not necessarily drawn to scale. Device 100 may include a substrate 110, an anode 115, a hole injection layer 120, a hole transport layer 125, an electron blocking layer 130, an emissive layer 135, a hole blocking layer 140, an electron transport layer 145, an electron injection layer 150, a protective layer 155, and a cathode 160. Cathode 160 is a compound cathode having a first conductive layer 162 and a second conductive layer 164. Device 100 may be fabricated by depositing the layers described, in order.

Substrate 110 may be any suitable substrate that provides desired structural properties. Substrate 110 may be flexible or rigid. Substrate 110 may be transparent, translucent or opaque. Plastic and glass are examples of preferred rigid substrate materials. Plastic and metal foils are examples of preferred flexible substrate materials. Substrate 110 may be a semiconductor material in order to facilitate the fabrication of circuitry. For example, substrate 110 may be a silicon wafer upon which circuits are fabricated, capable of controlling OLEDs subsequently deposited on the substrate. Other substrates may be used. The material and thickness of substrate 110 may be chosen to obtain desired structural and optical properties.

Anode 115 may be any suitable anode that is sufficiently conductive to transport holes to the organic layers. The material of anode 115 preferably has a work function higher than about 4 eV (a "high work function material"). Preferred anode materials include conductive metal oxides, such as indium tin oxide (ITO) and indium zinc oxide (IZO), aluminum zinc oxide (AlZnO), and metals. Anode 115 (and substrate 110) may be sufficiently transparent to create a bottom-emitting device. A preferred transparent substrate and anode combination is commercially available ITO (anode) deposited on glass or plastic (substrate). A flexible and transparent substrate-anode combination is disclosed in U.S. Pat. Nos. 5,844,363 and 6,602,540 B2, which are incorporated by reference in their entireties. Anode 115 may be opaque and/or reflective. A reflective anode 115 may be preferred for some top-emitting devices, to increase the amount of light emitted from the top of the device. The material and thickness of anode 115 may be chosen to obtain desired conductive and optical properties. Where anode 115 is transparent, there may be a range of thickness for a particular material that is thick enough to provide the desired conductivity, yet thin enough to provide the desired degree of transparency. Other anode materials and structures may be used.

Hole transport layer 125 may include a material capable of transporting holes. Hole transport layer 130 may be intrinsic (undoped), or doped. Doping may be used to enhance conductivity. α-NPD and TPD are examples of intrinsic hole transport layers. An example of a p-doped hole transport layer is m-MTDATA doped with $F_4$-TCNQ at a molar ratio of 50:1, as disclosed in United States Patent Application Publication No. 2003-0230980 to Forrest et al., which is incorporated by reference in its entirety. Other hole transport layers may be used.

Emissive layer 135 may include an organic material capable of emitting light when a current is passed between anode 115 and cathode 160. Preferably, emissive layer 135 contains a phosphorescent emissive material, although fluorescent emissive materials may also be used. Phosphorescent materials are preferred because of the higher luminescent efficiencies associated with such materials. Emissive layer 135 may also comprise a host material capable of transporting electrons and/or holes, doped with an emissive material that may trap electrons, holes, and/or excitons, such that excitons relax from the emissive material via a photoemissive mechanism. Emissive layer 135 may comprise a single material that combines transport and emissive properties. Whether the emissive material is a dopant or a major constituent, emissive layer 135 may comprise other materials, such as dopants that tune the emission of the emissive material. Emissive layer 135 may include a plurality of emissive materials capable of, in combination, emitting a desired spectrum of light. Examples of phosphorescent emissive materials include Ir(ppy)$_3$. Examples of fluorescent emissive materials include DCM and DMQA. Examples of host materials include Alq$_3$, CBP and mCP. Examples of emissive and host materials are disclosed in U.S. Pat. No. 6,303,238 to Thompson et al., which is incorporated by reference in its entirety. Emissive material may be included in emissive layer 135 in a number of ways. For example, an emissive small molecule may be incorporated into a polymer. This may be accomplished by several ways: by doping the small molecule into the polymer either as a separate and distinct molecular species; or by incorporating the small molecule into the backbone of the polymer, so as to form a co-polymer; or by bonding the small molecule as a pendant group on the polymer. Other emissive layer materials and structures may be used. For example, a small molecule emissive material may be present as the core of a dendrimer.

Many useful emissive materials include one or more ligands bound to a metal center. A ligand may be referred to as "photoactive" if it contributes directly to the photoactive properties of an organometallic emissive material. A "photoactive" ligand may provide, in conjunction with a metal, the energy levels from which and to which an electron moves when a photon is emitted. Other ligands may be referred to as "ancillary." Ancillary ligands may modify the photoactive properties of the molecule, for example by shifting the energy levels of a photoactive ligand, but ancillary ligands do not directly provide the energy levels involved in light emission. A ligand that is photoactive in one molecule may be ancillary in another. These definitions of photoactive and ancillary are intended as non-limiting theories.

Electron transport layer 145 may include a material capable of transporting electrons. Electron transport layer 145 may be intrinsic (undoped), or doped. Doping may be used to enhance conductivity. Alq$_3$ is an example of an intrinsic electron transport layer. An example of an n-doped electron transport layer is BPhen doped with Li at a molar ratio of 1:1, as disclosed in United States Patent Application Publication No. 2003-0230980 to Forrest et al., which is incorporated by reference in its entirety. Other electron transport layers may be used.

The charge carrying component of the electron transport layer may be selected such that electrons can be efficiently injected from the cathode into the LUMO (Lowest Unoccupied Molecular Orbital) energy level of the electron transport layer. The "charge carrying component" is the material responsible for the LUMO energy level that actually transports electrons. This component may be the base material, or it may be a dopant. The LUMO energy level of an organic material may be generally characterized by the electron affinity of that material and the relative electron injection efficiency of a cathode may be generally characterized in terms of the work function of the cathode material. This means that the preferred properties of an electron transport layer and the adjacent cathode may be specified in terms of the electron affinity of the charge carrying component of the ETL and the work function of the cathode material. In particular, so as to achieve high electron injection efficiency, the work function of the cathode material is preferably not greater than the electron affinity of the charge carrying component of the electron transport layer by more than about 0.75 eV, more preferably, by not more than about 0.5 eV. Similar considerations apply to any layer into which electrons are being injected.

Cathode 160 may be any suitable material or combination of materials known to the art, such that cathode 160 is capable of conducting electrons and injecting them into the organic layers of device 100. Cathode 160 may be transparent or opaque, and may be reflective. Metals and metal oxides are examples of suitable cathode materials. Cathode 160 may be a single layer, or may have a compound structure. FIG. 1 shows a compound cathode 160 having a thin metal layer 162 and a thicker conductive metal oxide layer 164. In a compound cathode, preferred materials for the thicker layer 164 include ITO, IZO, and other materials known to the art. U.S. Pat. Nos. 5,703,436, 5,707,745, 6,548,956 B2 and 6,576,134 B2, which are incorporated by reference in their entireties, disclose examples of cathodes including compound cathodes having a thin layer of metal such as Mg:Ag with an overlying transparent, electrically-conductive, sputter-deposited ITO layer. The part of cathode 160 that is in contact with the underlying organic layer, whether it is a single layer cathode 160, the thin metal layer 162 of a compound cathode, or some other part, is preferably made of a material having a work function lower than about 4 eV (a "low work function material"). Other cathode materials and structures may be used.

Blocking layers may be used to reduce the number of charge carriers (electrons or holes) and/or excitons that leave the emissive layer. An electron blocking layer 130 may be disposed between emissive layer 135 and the hole transport layer 125, to block electrons from leaving emissive layer 135 in the direction of hole transport layer 125. Similarly, a hole blocking layer 140 may be disposed between emissive layer 135 and electron transport layer 145, to block holes from leaving emissive layer 135 in the direction of electron transport layer 145. Blocking layers may also be used to block excitons from diffusing out of the emissive layer. The theory and use of blocking layers is described in more detail in U.S. Pat. No. 6,097,147 and United States Patent Application Publication No. 2003-0230980 to Forrest et al., which are incorporated by reference in their entireties.

As used herein, and as would be understood by one skilled in the art, the term "blocking layer" means that the layer provides a barrier that significantly inhibits transport of charge carriers and/or excitons through the device, without suggesting that the layer necessarily completely blocks the charge carriers and/or excitons. The presence of such a blocking layer in a device may result in substantially higher efficiencies as compared to a similar device lacking a blocking layer. Also, a blocking layer may be used to confine emission to a desired region of an OLED.

Generally, injection layers are comprised of a material that may improve the injection of charge carriers from one layer, such as an electrode or an organic layer, into an adjacent organic layer. Injection layers may also perform a charge transport function. In device 100, hole injection layer 120 may be any layer that improves the injection of holes from anode 115 into hole transport layer 125. CuPc is an example of a material that may be used as a hole injection layer from an ITO anode 115, and other anodes. In device 100, electron injection layer 150 may be any layer that improves the injection of electrons into electron transport layer 145. LiF/Al is an example of a material that may be used as an electron injection layer into an electron transport layer from an adjacent layer. Other materials or combinations of materials may be used for injection layers. Depending upon the configuration of a particular device, injection layers may be disposed at locations different than those shown in device 100. More examples of injection layers are provided in U.S. patent application Ser. No. 09/931,948 to Lu et al., which is incorporated by reference in its entirety. A hole injection layer may comprise a solution deposited material, such as a spin-coated polymer, e.g., PEDOT:PSS, or it may be a vapor deposited small molecule material, e.g., CuPc or MTDATA.

A hole injection layer (HIL) may planarize or wet the anode surface so as to provide efficient hole injection from the anode into the hole injecting material. A hole injection layer may also have a charge carrying component having HOMO (Highest Occupied Molecular Orbital) energy levels that favorably match up, as defined by their herein-described relative ionization potential (IP) energies, with the adjacent anode layer on one side of the HIL and the hole transporting layer on the opposite side of the HIL. The "charge carrying component" is the material responsible for the HOMO energy level that actually transports holes. This component may be the base material of the HIL, or it may be a dopant. Using a doped HIL allows the dopant to be selected for its electrical properties, and the host to be selected for morphological properties such as wetting, flexibility, toughness, etc. Preferred properties for the HIL material are such that holes can be efficiently injected from the anode into the HIL material. In particular, the charge carrying component of the HIL preferably has an IP not more than about 0.7 eV greater that the IP of the anode material. More preferably, the charge carrying component has an IP not more than about 0.5 eV greater than the anode material. Similar considerations apply to any layer into which holes are being injected. HIL materials are further distinguished from conventional hole transporting materials that are typically used in the hole transporting layer of an OLED in that such HIL materials may have a hole conductivity that is substantially less than the hole conductivity of conventional hole transporting materials. The thickness of the HIL of the present invention may be thick enough to help planarize or wet the surface of the anode layer. For example, an HIL thickness of as little as 10 nm may be acceptable for a very smooth anode surface. However, since anode surfaces tend to be very rough, a thickness for the HIL of up to 50 nm may be desired in some cases.

A protective layer may be used to protect underlying layers during subsequent fabrication processes. For example, the processes used to fabricate metal or metal oxide top electrodes may damage organic layers, and a protective layer may be used to reduce or eliminate such damage. In device 100, protective layer 155 may reduce damage to underlying organic layers during the fabrication of cathode 160. Preferably, a protective layer has a high carrier mobility for the type of carrier that it transports (electrons in device 100), such that it does not significantly increase the operating voltage of device 100. CuPc, BCP, and various metal phthalocyanines are examples of materials that may be used in protective layers. Other materials or combinations of materials may be used. The thickness of protective layer 155 is preferably thick enough that there is little or no damage to underlying layers due to fabrication processes that occur after organic protective layer 160 is deposited, yet not so thick as to significantly increase the operating voltage of device 100. Protective layer 155 may be doped to increase its conductivity. For example, a CuPc or BCP protective layer 160 may be doped with Li. A more detailed description of protective layers may be found in U.S. patent application Ser. No. 09/931,948 to Lu et al., which is incorporated by reference in its entirety.

Figure 2:
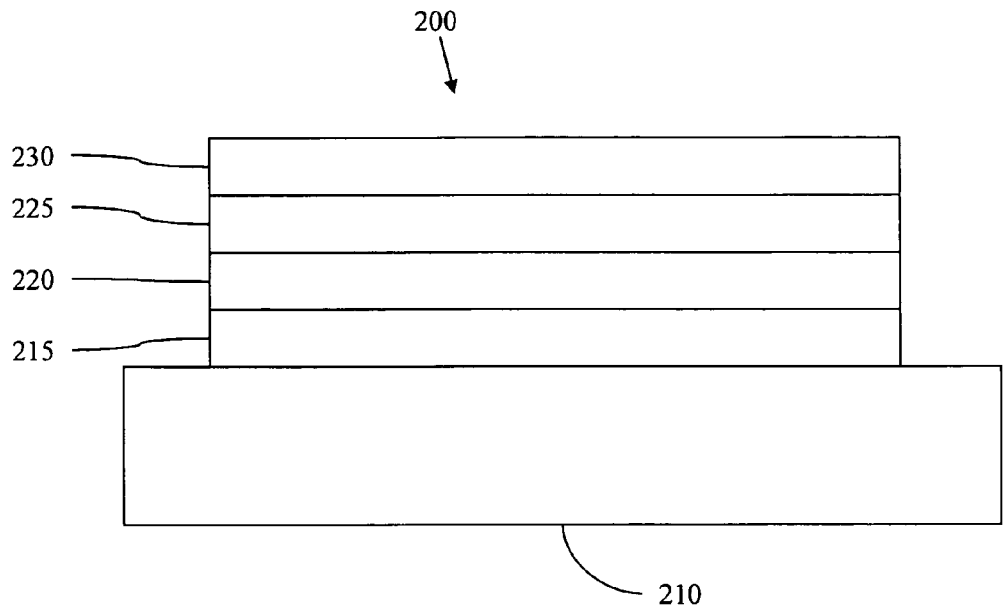
FIG. 2 shows an inverted organic light emitting device that does not have a separate electron transport layer.

FIG. 2 shows an inverted OLED 200. The device includes a substrate 210, an cathode 215, an emissive layer 220, a hole transport layer 225, and an anode 230. Device 200 may be fabricated by depositing the layers described, in order. Because the most common OLED configuration has a cathode disposed over the anode, and device 200 has cathode 215 disposed under anode 230, device 200 may be referred to as an "inverted" OLED. Materials similar to those described with respect to device 100 may be used in the corresponding layers of device 200. FIG. 2 provides one example of how some layers may be omitted from the structure of device 100.

The simple layered structure illustrated in FIGS. 1 and 2 is provided by way of non-limiting example, and it is understood that embodiments of the invention may be used in connection with a wide variety of other structures. The specific materials and structures described are exemplary in nature, and other materials and structures may be used. Functional OLEDs may be achieved by combining the various layers described in different ways, or layers may be omitted entirely, based on design, performance, and cost factors. Other layers not specifically described may also be included. Materials other than those specifically described may be used. Although many of the examples provided herein describe various layers as comprising a single material, it is understood that combinations of materials, such as a mixture of host and dopant, or more generally a mixture, may be used. Also, the layers may have various sublayers. The names given to the various layers herein are not intended to be strictly limiting. For example, in device 200, hole transport layer 225 transports holes and injects holes into emissive layer 220, and may be described as a hole transport layer or a hole injection layer. In one embodiment, an OLED may be described as having an "organic layer" disposed between a cathode and an anode. This organic layer may comprise a single layer, or may further comprise multiple layers of different organic materials as described, for example, with respect to FIGS. 1 and 2.

Structures and materials not specifically described may also be used, such as OLEDs comprised of polymeric materials (PLEDs) such as disclosed in U.S. Pat. No. 5,247,190, Friend et al., which is incorporated by reference in its entirety. By way of further example, OLEDs having a single organic layer may be used. OLEDs may be stacked, for example as described in U.S. Pat. No. 5,707,745 to Forrest et al, which is incorporated by reference in its entirety. The OLED structure may deviate from the simple layered structure illustrated in FIGS. 1 and 2. For example, the substrate may include an angled reflective surface to improve out-coupling, such as a mesa structure as described in U.S. Pat. No. 6,091,195 to Forrest et al., and/or a pit structure as described in U.S. Pat. No. 5,834,893 to Bulovic et al., which are incorporated by reference in their entireties.

Unless otherwise specified, any of the layers of the various embodiments may be deposited by any suitable method. For the organic layers, preferred methods include thermal evaporation, ink-jet, such as described in U.S. Pat. Nos. 6,013,982 and 6,087,196, which are incorporated by reference in their entireties, organic vapor phase deposition (OVPD), such as described in U.S. Pat. No. 6,337,102 to Forrest et al., which is incorporated by reference in its entirety, and deposition by organic vapor jet printing (OVJP), such as described in U.S. patent application Ser. No. 10/233,470, which is incorporated by reference in its entirety. Other suitable deposition methods include spin coating and other solution based processes. Solution based processes are preferably carried out in nitrogen or an inert atmosphere. For the other layers, preferred methods include thermal evaporation. Preferred patterning methods include deposition through a mask, cold welding such as described in U.S. Pat. Nos. 6,294,398 and 6,468,819, which are incorporated by reference in their entireties, and patterning associated with some of the deposition methods such as ink-jet and OVJP. Other methods may also be used. The materials to be deposited may be modified to make them compatible with a particular deposition method. For example, substituents such as alkyl and aryl groups, branched or unbranched, and preferably containing at least 3 carbons, may be used in small molecules to enhance their ability to undergo solution processing. Substituents having 20 carbons or more may be used, and 3-20 carbons is a preferred range. Materials with asymmetric structures may have better solution processibility than those having symmetric structures, because asymmetric materials may have a lower tendency to recrystallize. Dendrimer substituents may be used to enhance the ability of small molecules to undergo solution processing.

The molecules disclosed herein may be substituted in a number of different ways without departing from the scope of the invention. For example, substituents may be added to a compound having three bidentate ligands, such that after the substituents are added, one or more of the bidentate ligands are linked together to form, for example, a tetradentate or hexadentate ligand. Other such linkages may be formed. It is believed that this type of linking may increase stability relative to a similar compound without linking, due to what is generally understood in the art as a "chelating effect."

Devices fabricated in accordance with embodiments of the invention may be incorporated into a wide variety of consumer products, including flat panel displays, computer monitors, televisions, billboards, lights for interior or exterior illumination and/or signaling, heads up displays, fully transparent displays, flexible displays, laser printers, telephones, cell phones, personal digital assistants (PDAs), laptop computers, digital cameras, camcorders, viewfinders, micro-displays, vehicles, a large area wall, theater or stadium screen, or a sign. Various control mechanisms may be used to control devices fabricated in accordance with the present invention, including passive matrix and active matrix. Many of the devices are intended for use in a temperature range comfortable to humans, such as 18 degrees C. to 30 degrees C., and more preferably at room temperature (20-25 degrees C.).

The materials and structures described herein may have applications in devices other than OLEDs. For example, other optoelectronic devices such as organic solar cells and organic photodetectors may employ the materials and structures. More generally, organic devices, such as organic transistors, may employ the materials and structures.

In one aspect, certain iridium compounds are provided. The iridium compounds comprise an iridium(III)-ligand complex having the general formula: (C^N)₂—Ir—(N^N). (C^N) and (N^N) may each represent a ligand coordinated to an iridium atom.

In certain instances, the iridium compound can be represented by the formula:

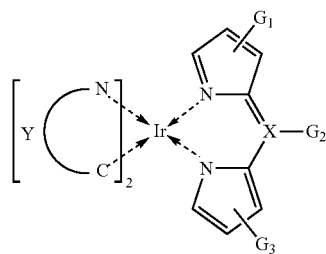

In these instances, the (N^N) ligand is represented by a dipyrrin moiety comprising two pyrrole rings. Each pyrrole ring in the dipyrrin moiety may be substituted at any position by substituents G₁ and G₃.

In certain instances, G₁ and G₃ may be a hydrogen, an aryl moiety, or a heteroaryl moiety. The term "aryl moiety" as used herein refers to structures containing at least one aromatic ring, including single-ring groups and polycyclic ring systems. The polycyclic rings may have two or more rings in which two atoms are common by two adjoining rings (the rings are "fused") wherein at least one of the rings is aromatic. Aryl moieties suitable for use as substituents G₁ or G₃ include the following examples (which may themselves, also be substituted):

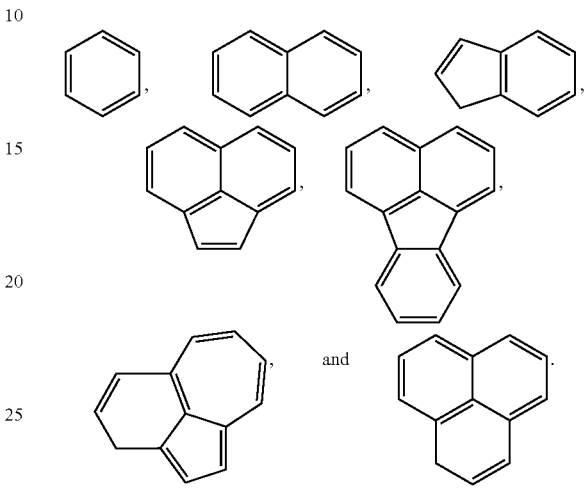

The term "heteroaryl moiety" as used herein contemplates single-ring heteroaromatic groups that may include from one to four heteroatoms. Examples of heteroaryl moieties include pyrrole, furan, thiophene, imidazole, oxazole, thiazole, triazole, tetrazole, pyrazole, pyridine, pyrazine, and pyrimidine, and the like. The term "heteroaryl moiety" also includes polycyclic heteroaromatic systems having two or more rings in which two atoms are common to two adjoining rings (the rings are "fused") wherein at least one of the rings is a heteroaryl. The other rings can be cycloalkyls, cycloalkenyls, aryl, heterocycles and/or heteroaryls. Heteroaryl moieties which may be suitable for use as substituents G₁ or G₃ include the following examples (which may themselves, also be substituted):

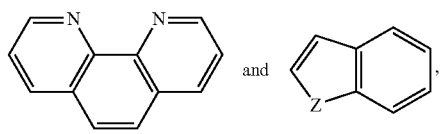

wherein Z may be S, O, NH, or NR$_A$, and wherein R$_A$ may be any alkyl moiety.

The term "alkyl moiety" as used herein contemplates both straight and branched alkyl chains. Preferred alkyl moieties are those containing from one to fifteen carbon atoms and includes methyl, ethyl, propyl, isopropyl, butyl, isobutyl, tertbutyl, and the like. Additionally, the alkyl moieties themselves may be substituted with one or more substituents.

Substituent G₂ may be a hydrogen, phenyl, substituted phenyl, or alkyl. The substituted phenyl may have any of various substituents, including halogens (e.g., F or I), CHO, CN, COOR$_B$, ORB, t-butyl, boron-containing groups such as 4,4,5,5-tetramethyl-1,3,2-dioxaborolane, or R$_B$, wherein R$_B$ is an alkyl. For example, the substituted phenyl may be mesityl. X may be a nitrogen or carbon atom. In certain instances, any of G₁, G₂, or G₃ may be fused to a pyrrole ring on the dipyrrin moiety. The resulting fused ring system may have alternating or non-alternating conjugation.
Various moieties suitable for use as the (N^N) ligand include the following:
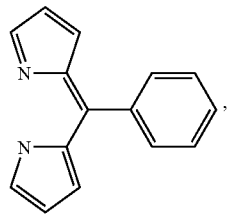,
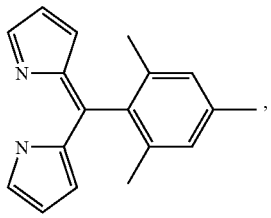,
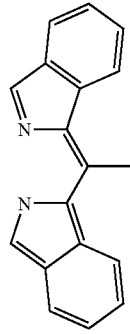,
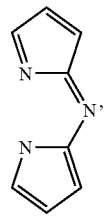,
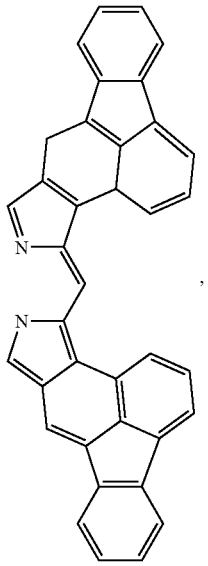,
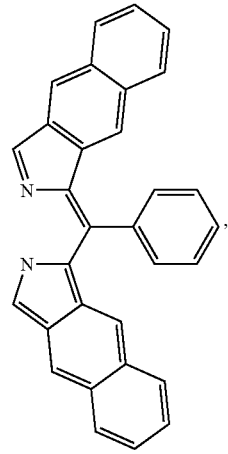,
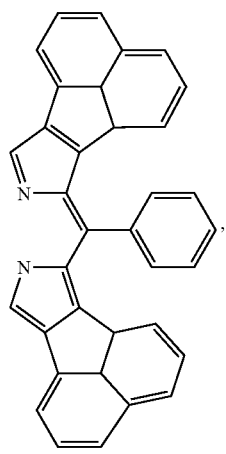,
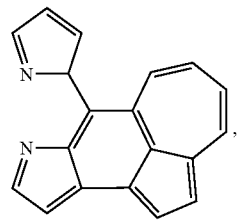,
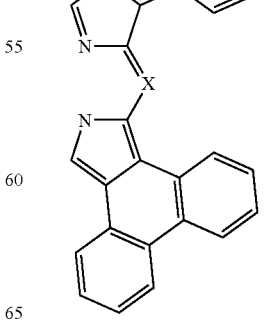,
-continued
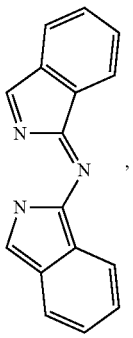,
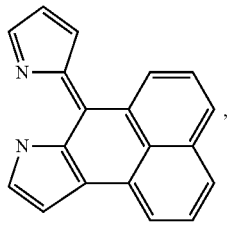,
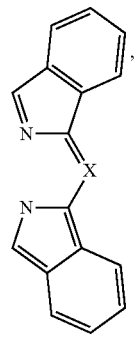,
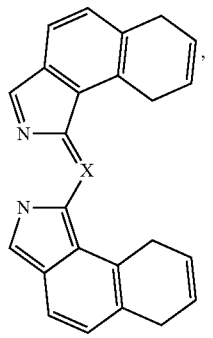,
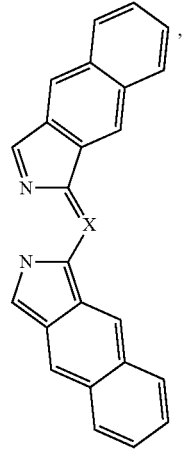,
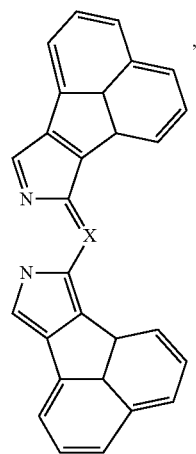,
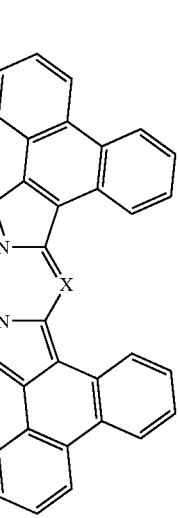,
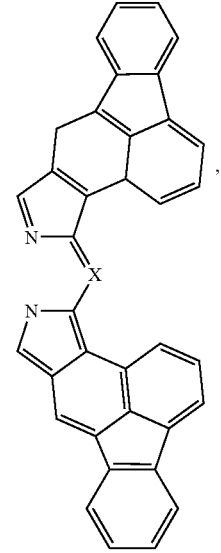,

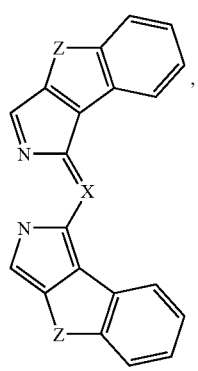 , and 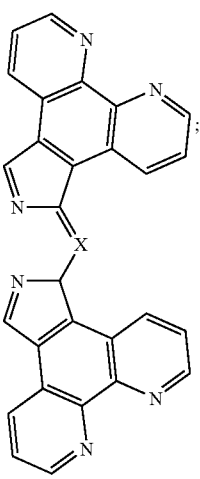 ;

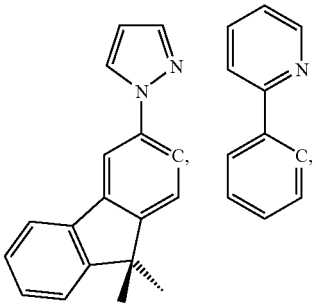

"flpz"    "ppy"    "pq"

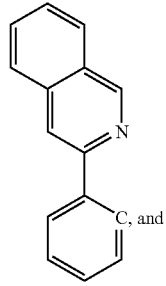

"dpo"

wherein Z may be S, O, NH, or $NR_4$, and wherein $R_4$ may be any alkyl moiety.

The (C^N) ligand, represented as

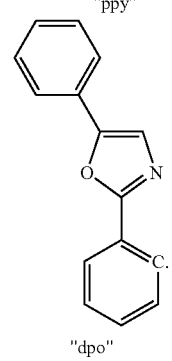

may contain a phenylpyrazole moiety, phenylpyridine moiety, or phenyloxazol moiety.

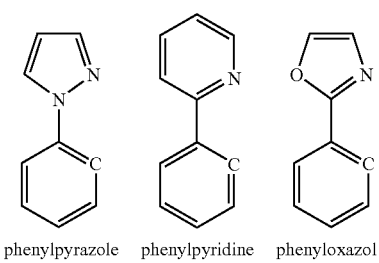

phenylpyrazole    phenylpyridine    phenyloxazol

The constituent rings of the (C^N) ligand may have one or more of various substitutions at any position on the rings. For example, suitable (C^N) ligands include the following:

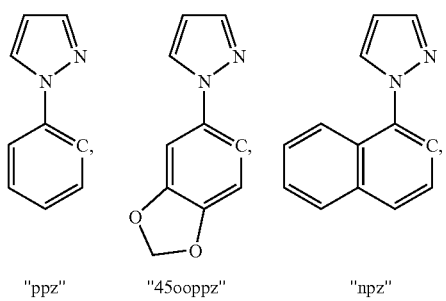

"ppz"    "45ooppz"    "npz"

In certain instances, the iridium compound may have a primary phosphorescent photoluminescence peak wavelength in the near-infrared (IR) range. Preferably, the photoluminescence peak wavelength is greater than 680 nm.

Without intending to be bound by theory, in these instances, it is believed that (C^N) may be an ancillary cyclometallating ligand and (N^N) may be a photoactive ligand. As such, the (N^N) ligand may directly influence the emission spectra of the iridium compounds, whereas variations in the (C^N) ligand may have minimal effect. Thus, in certain instances, the substituents $G_1$, $G_2$, and $G_3$, as well as X, may be selected such that the iridium compound has a primary phosphorescent photoluminescence peak wavelength in the near-infrared (IR) spectrum.

Without intending to be bound by theory, the (C^N) ligand may have an effect on the oxidation-reduction properties of the iridium compounds. Thus, in certain instances, the (C^N) ligand may be selected to obtain a desired oxidation-reduction property of the iridium compound, such as reversible oxidation. For example, the (C^N) ligand may have substitution groups containing electron-donating atoms such as oxygen or nitrogen.

One of ordinary skill in the art will be able to make any of the iridium compounds disclosed herein using any of various synthesis techniques.

The iridium compounds disclosed herein have applications in organic electronic devices. Thus, in another aspect, organic devices that use certain iridium compounds are provided. The organic device may comprise an organic layer and the organic layer may comprise any of the iridium compounds disclosed herein. The organic device may be an electronic device such as a light-emitting diode, field-effect transistor, photovoltaic device, and the like. In organic light-emitting diodes, the organic layer may be an emissive layer, wherein the iridium compounds serve as dopants.

In another aspect, organic devices that use certain metalloporphyrin compounds are provided. The organic device may comprise an organic layer and the organic layer may comprise any of the metalloporphyrin compounds disclosed herein. The organic device may be an electronic device such as a light-emitting diode, field-effect transistor, photovoltaic device, and the like. In organic light-emitting diodes, the organic layer may be an emissive layer, wherein the metalloporphyrin compounds serve as dopants.

In certain instances, the metalloporphyrin compounds have the formula:

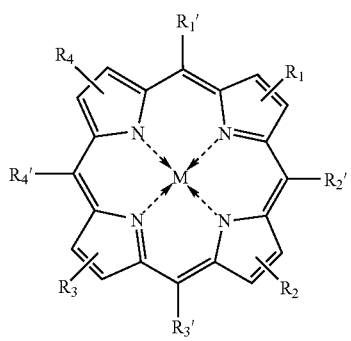

In these instances, the metalloporphyrin compounds comprise a core porphyrin structure with four pyrrole rings. A metal M is in coordination with the core porphyrin structure in its central cavity. The metal M may be any metal capable of combining with the core porphyrin structure, including platinum, palladium, iridium, iron, zinc, and copper.

Each pyrrole ring of the core porphyrin structure may be substituted at any position by substituents $R_1$-$R_4$. In certain instances, each of $R_1$-$R_4$ may be an aliphatic moiety, aryl moiety, heteroaryl moiety, or macrocycle moiety. The term "aliphatic moiety" as used herein refers to any non-aromatic chain arrangement of carbon atoms, whether straight, branched, or cyclic. An aliphatic moiety may include alkanes, alkenes, or alkynes. Preferred aliphatic moieties are those containing 1 to 15 carbon atoms. The term "macrocycle" as used herein refers to a heterocyclic macromolecule having three or more potential donor atoms in a ring of at least nine atoms. The rings in a macrocycle may be aromatic or non-aromatic.

For example, each $R_1$-$R_4$ may be one of the following aryl or heteroaryl moieties:

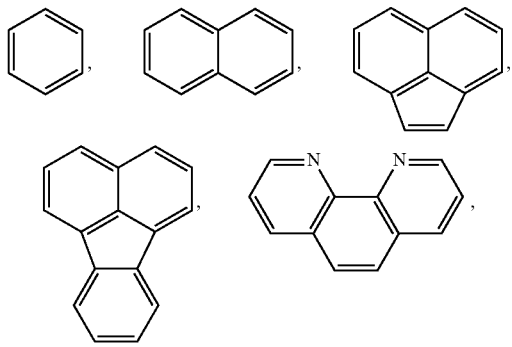

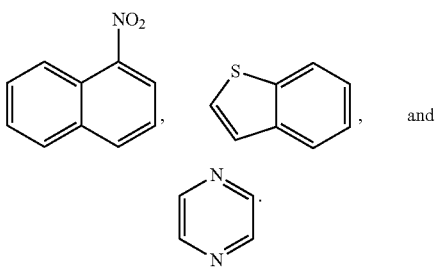

The aryl moieties or heteroaryl moieties may be fused to the adjoining pyrrole rings. Each of $R_1'$-$R_4'$ may be a hydrogen, phenyl, mesityl, or methyl.

Examples of metalloporphyrin compounds include the following:

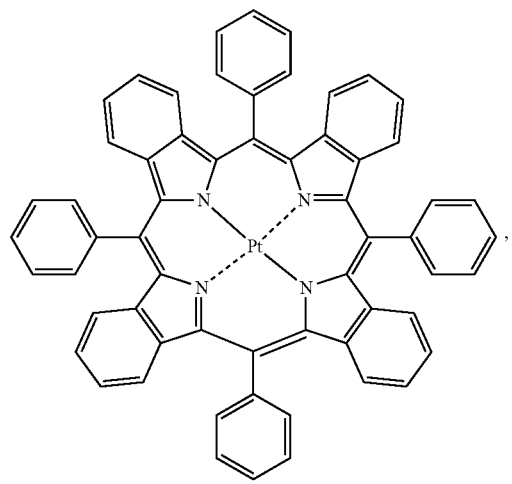

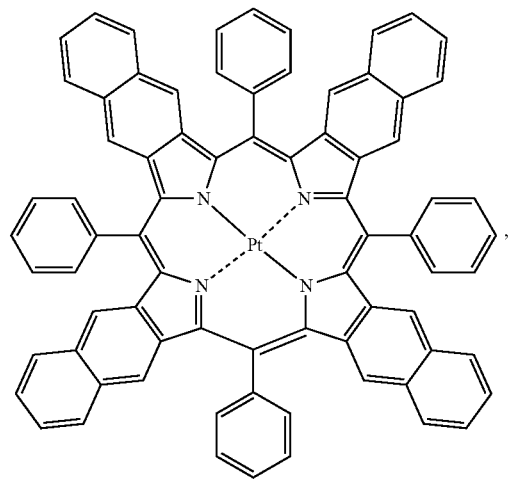

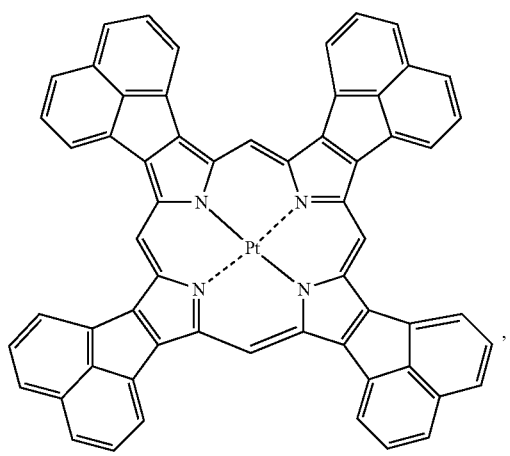
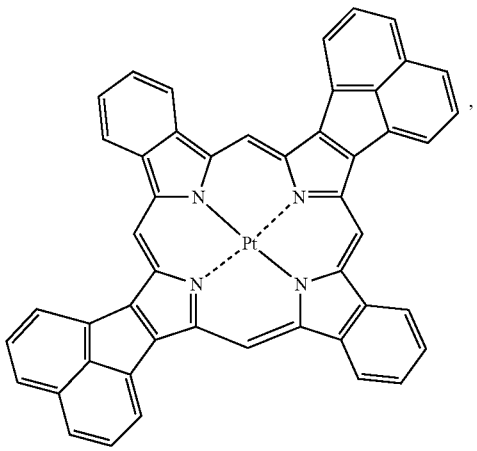
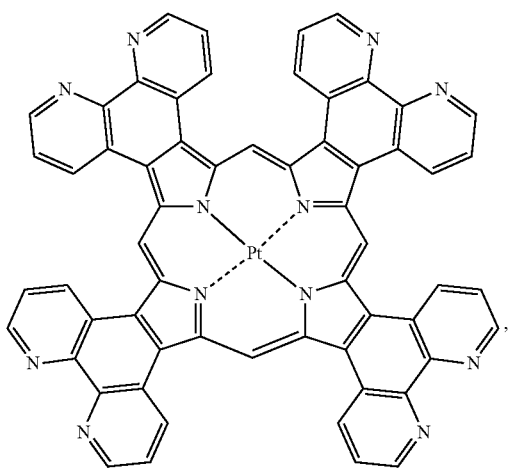
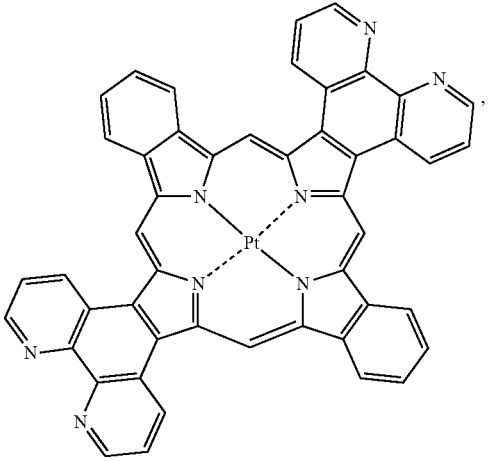
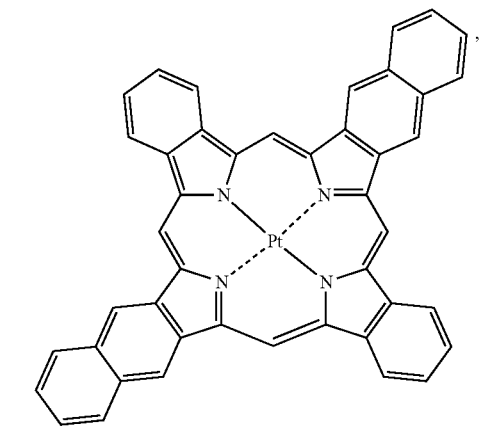
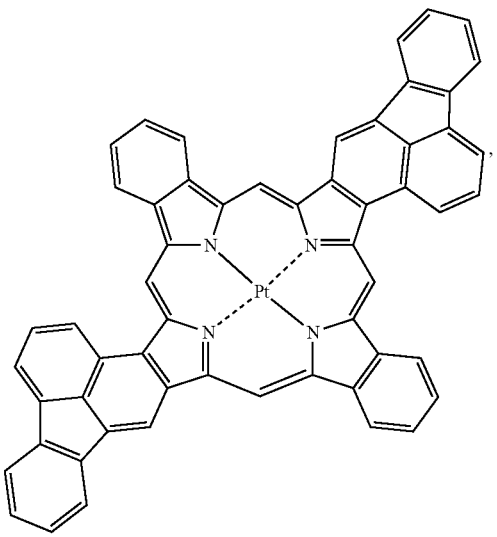

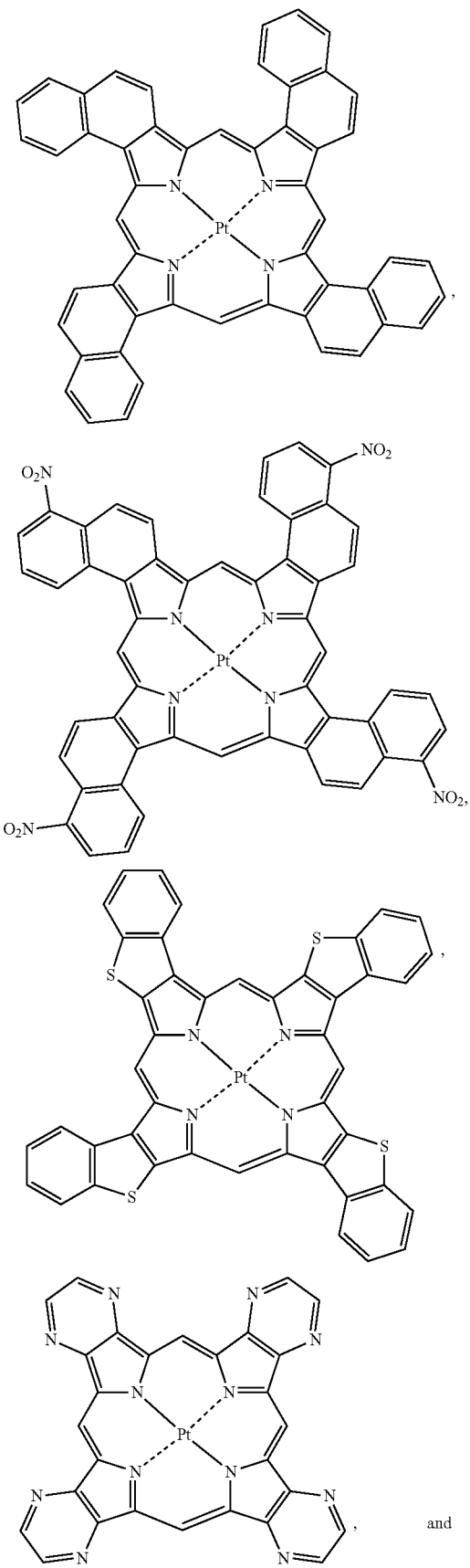

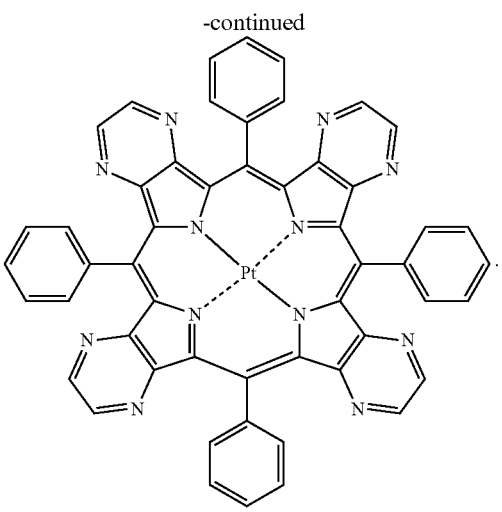

Without intending to be bound by theory, it is believed that enlarging the ring system on the core porphyrin structure or increasing the conjugated π-electron system of the pyrrole rings can influence the photoluminescence emission spectrum of the metalloporphyrin compound. Thus, in certain instances, each of the substituents $R_1$-$R_4$ and $R_1'$-$R_4'$, as well as metal M, may be selected such that the metalloporphyrin compound has a primary phosphorescent photoluminescence peak wavelength in the near-infrared range. Preferably, the photoluminescence peak wavelength is greater than 680 nm.

In certain instances, the primary phosphorescent photoluminescence emission peak of the metalloporphyrin compound has a narrow bandwidth. In some instances, the bandwidth (measured full-width at half-maximum) may be less than 60 nm, and preferably, less than 35 nm. Without intending to be bound by theory, it is believed that the bandwidth may be narrowed by increasing the molecular symmetry of the metalloporphyrin compound. Thus, in certain instances, each of the substituents $R_1$-$R_4$ and $R_1'$-$R_4'$ may be selected such that the metalloporphyrin compound has at least one axis of molecular symmetry. The axis of molecular symmetry may be a rotational axis or mirror-image axis. For example, such symmetry may be obtained where $R_1$ is the same as $R_3$, or where $R_2$ is the same as $R_4$, or where $R_1$-$R_4$ are all the same.

Without intending to be bound by theory, it is believed that the quantum efficiency of the metalloporphyrin compound can be increased by increasing the rigidity of the core porphyrin structure and/or reducing the probability of non-radiative quenching mechanisms such as C—H bond vibrations. Thus, in certain embodiments, each of substituents $R_1$-$R_4$ and $R_1'$-$R_4'$ may be selected such that the metalloporphyrin compound exhibits increased quantum efficiency.

Without intending to be bound by theory, it is believed that emissive layers using certain metalloporphyrin compounds as the dopant may have improved luminescence capabilities by harvesting energy from the host material and becoming sensitized by exchange energy transfer from the ligand-based triplet state. Thus, in certain instances, where the metalloporphyrin compound is used as a dopant in an emissive layer, the absorption spectrum of the metalloporphyrin compound overlaps with the emission spectrum of the host material. This overlap may maximize the probability of a Forster energy transfer. For example, the metalloporphyrin compound may quench the emission of an $Alq_3$ host material. In some cases, the metalloporphyrin compound may completely quench the emission of the $Alq_3$ host material.

One of ordinary skill in the art will be able to make any of the metalloporphyrin compounds disclosed herein using any of various synthesis techniques.

EXAMPLES

Various possible iridium compounds, which are representative embodiments of the present invention, will now be described. It is understood that the specific methods, materials, conditions, process parameters, apparatus and the like do not necessarily limit the scope of the invention.

Examples Obtained by Synthesis

The following compounds were synthesized:

Example A

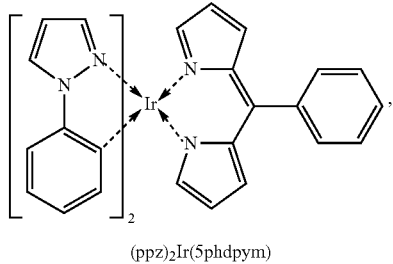

(ppz)$_2$Ir(5phdpym)

Example B

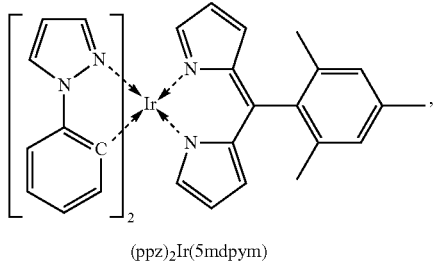

(ppz)$_2$Ir(5mdpym)

Example C

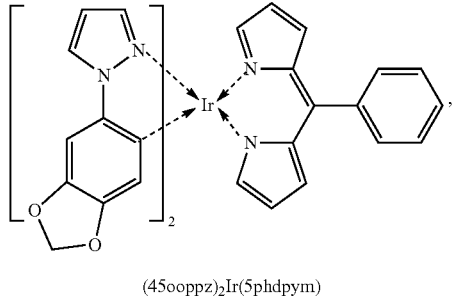

(45ooppz)$_2$Ir(5phdpym)

Example D

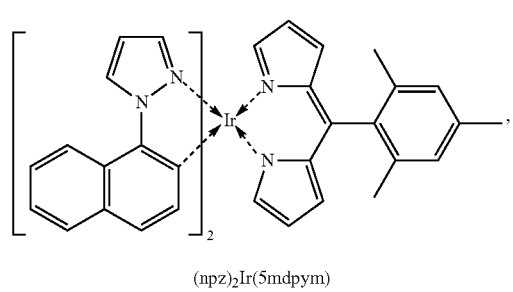

(npz)$_2$Ir(5mdpym)

Example E

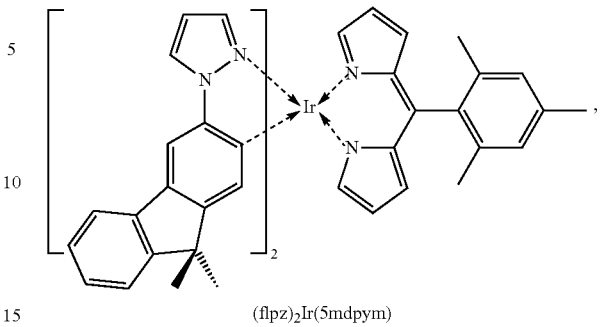

(flpz)$_2$Ir(5mdpym)

Example F

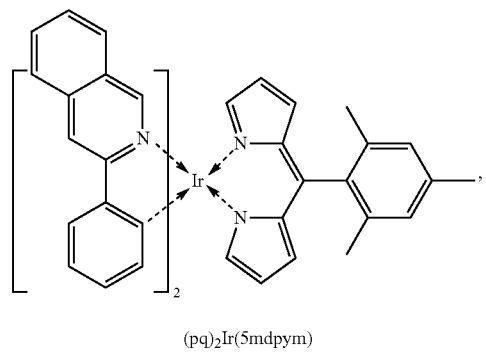

(pq)$_2$Ir(5mdpym)

Example G

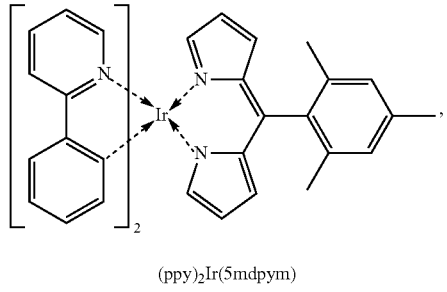

(ppy)$_2$Ir(5mdpym)

Example H

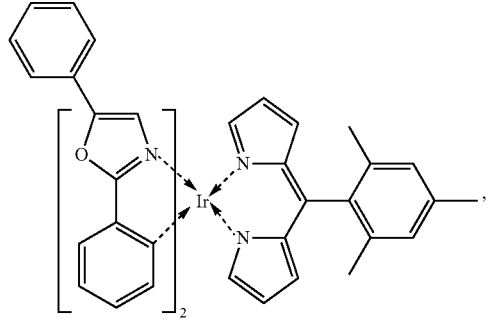

(dpo)$_2$Ir(5mdpym)

Example I

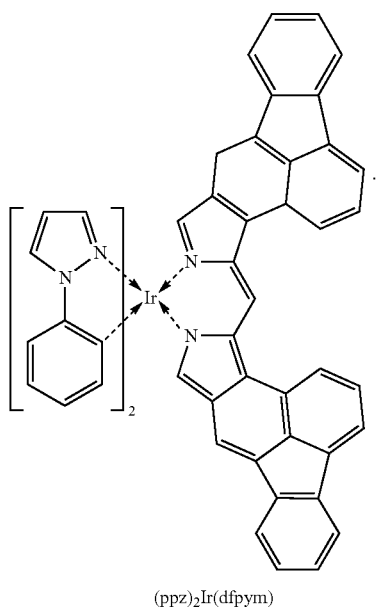

(ppz)₂Ir(dfpym)

Figure 3:
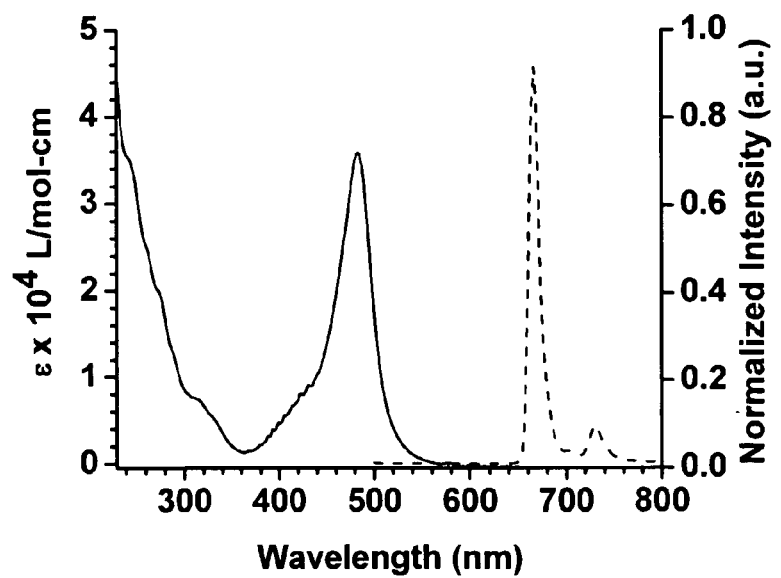
FIG. 3 shows the absorption and 77K emission spectra of compound Example A.
Figure 4:
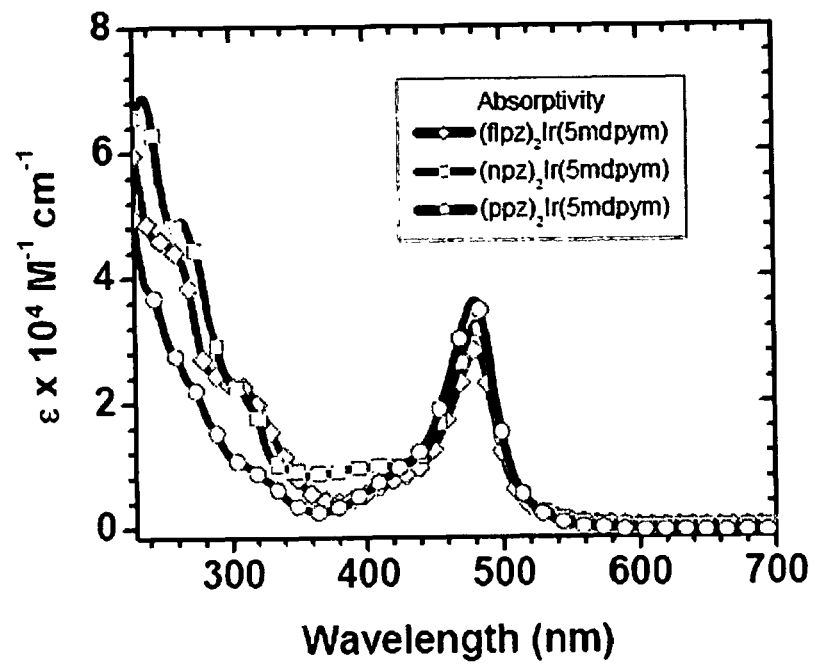
FIG. 4 shows the absorption spectra of various example iridium compounds.
Figure 5:
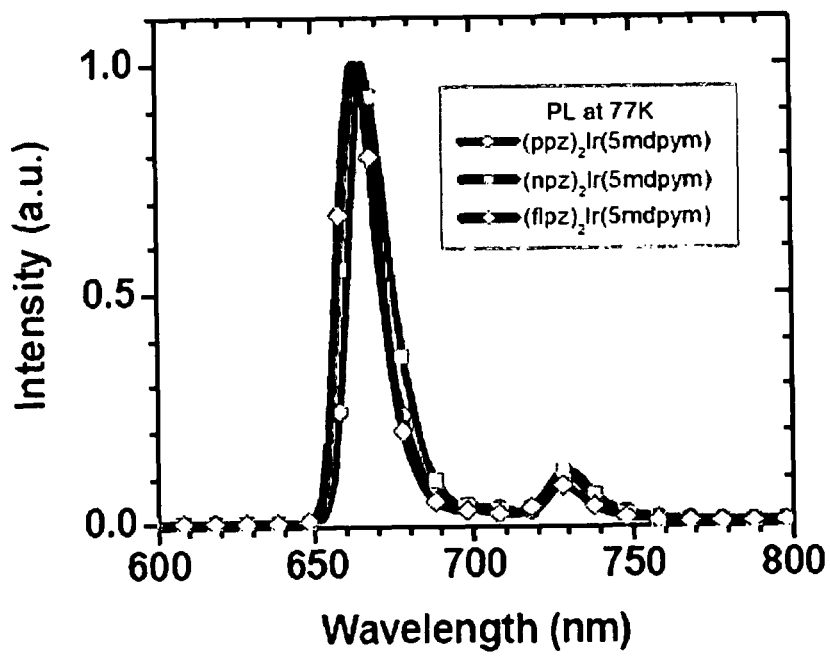
FIG. 5 shows the photoluminescence spectra of various example iridium compounds.
Figure 6:
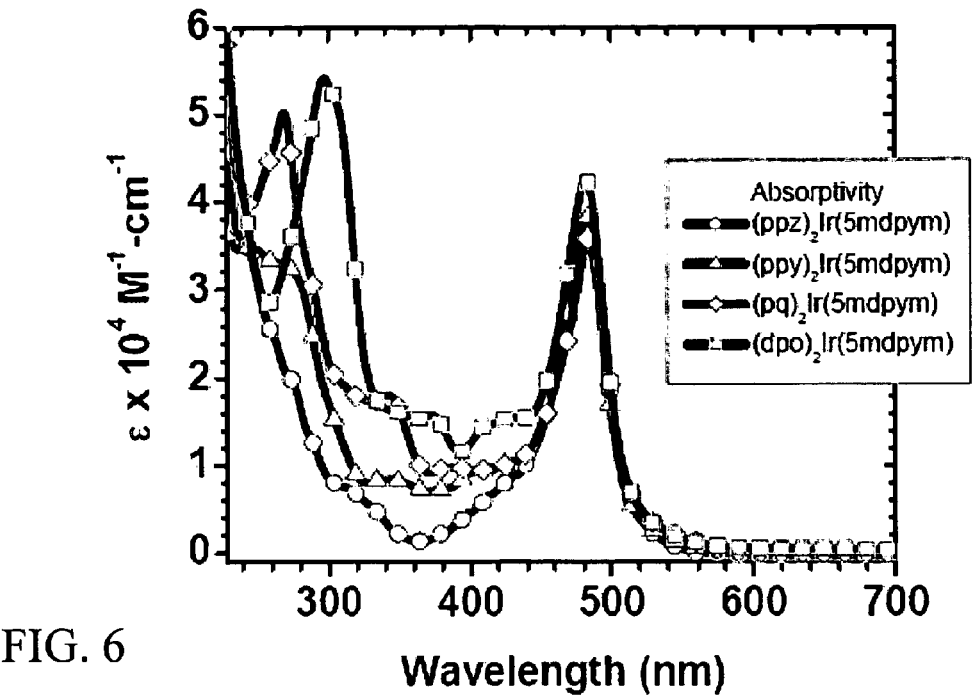
FIG. 6 shows the absorption spectra of various example iridium compounds.
Figure 7:
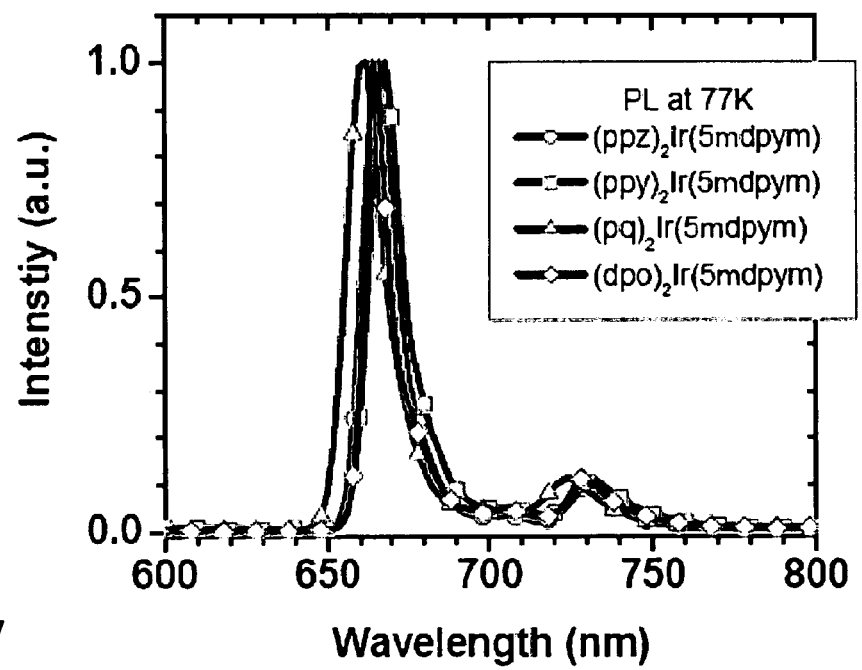
FIG. 7 shows the photoluminescence spectra of various example iridium compounds.

FIG. 3 shows the absorption and 77K emission spectra of compound Example A. The 77K phosphorescent emission of Example A is 666 nm with a lifetime of 25.5 μs. The room temperature phosphorescent emission (not shown) is red-shifted to 672 nm with a lifetime of 13.6 μs. FIGS. 4-7 show the absorption and 77K emission spectra of various iridium compound examples.

Figure 8:
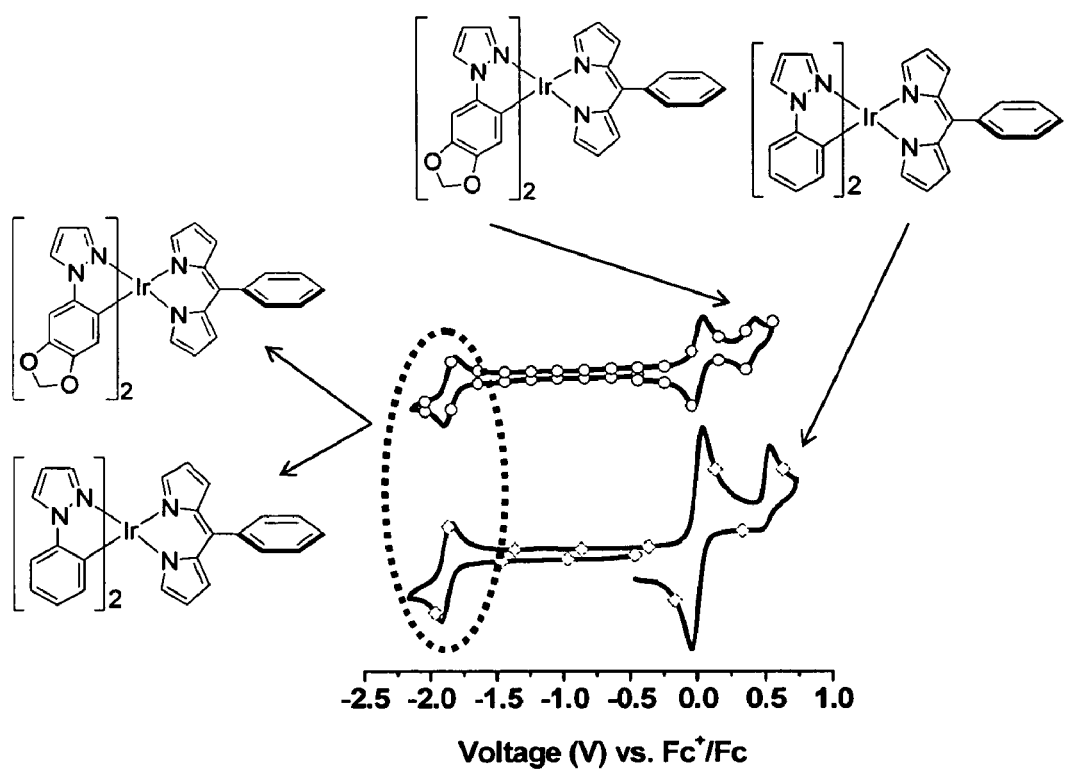
FIG. 8 shows cyclic voltammogram tracings of compound Examples A and C.

The electrochemical properties of all the above iridium compounds were examined. FIG. 8 shows cyclic voltammogram tracings for compound Examples A and C. Excluding compound Example C, all molecules exhibit reversible reduction and irreversible oxidation processes that occur at nearly the same potential. Compound Example C has a similar reduction potential, but exhibits reversible oxidation at a potential of 0.39 V, which is 130 mV lower than Example A This is believed to be due to the electron-donating atoms on the 4' and 5' positions on the phenyl ring in the (C^N) ligand. As such, in Example C, the oxidation process may involve the metal and the (C^N) ligand, and not the dipyrrin moiety.

Figure 9:
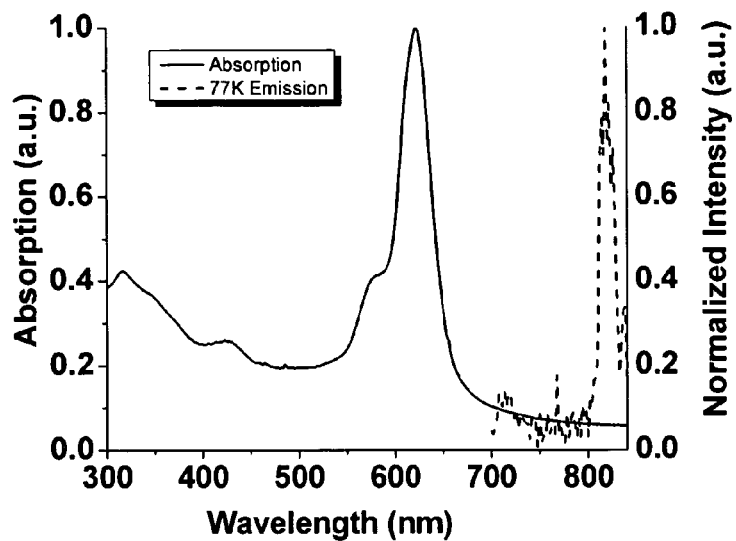
FIG. 9 shows the absorption and 77K emission spectra of compound Example I.

FIG. 9 shows the absorption and emission spectra of compound Example I. The 77K phosphorescent emission of Example I is 822 nm. At room temperature (not shown), the emission is red-shifted to 838 nm.

It is believed that DFT (Density Function Theory) calculations can provide accurate predictions of the spectral characteristics of bis-cyclometalated iridium(III) dipyrrin complexes. To verify the accuracy of DFT calculations on the iridium compounds disclosed herein, Examples A and I were subject to DFT calculation using the Titan software package (Wavefunction, Inc.) at the B3LYP/LACVP** level. For Example A, the calculated emission peak of 672 nm is identical to that obtained by experimental measurement. In Example I, the calculated emission peak of 820 is in strong agreement with the 838 nm obtained by experimental measurement. These results, which are summarized in Table 1 below, demonstrate that DFT calculations can predict the spectral characteristics of the iridium compounds disclosed herein with high accuracy.

TABLE 1

DFT Calculations for Examples A and I.

| Compound | HOMO | LUMO | HSOMO | [a]Singlet gap | [b]Triplet gap | [c]Triplet gap (nm) |
|---|---|---|---|---|---|---|
| A | −4.981 | −1.767 | −3.135 | 3.214 | 1.846 | 672 |
| I | −4.758 | −2.252 | −3.246 | 2.506 | 1.512 | 820 |

[a]HOMO-LUMO;
[b]HSOMO-HOMO;
[c](1240/T.G. nm)

Derivative Examples Obtained by DFT Calculations

Thus, sample DFT calculations were performed for other possible iridium compounds, which represent other embodiments of the present invention:

Example J

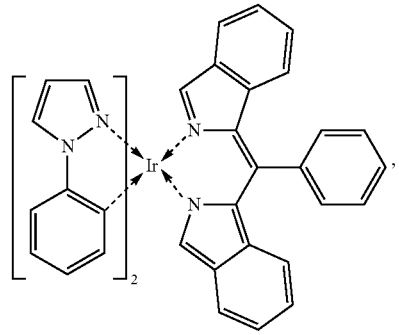

Example K

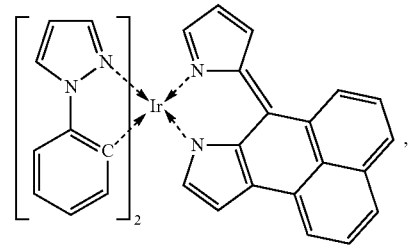

Example L

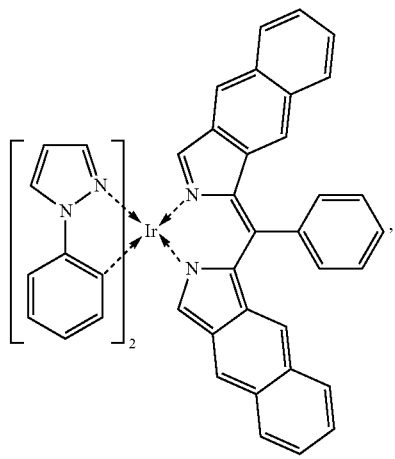

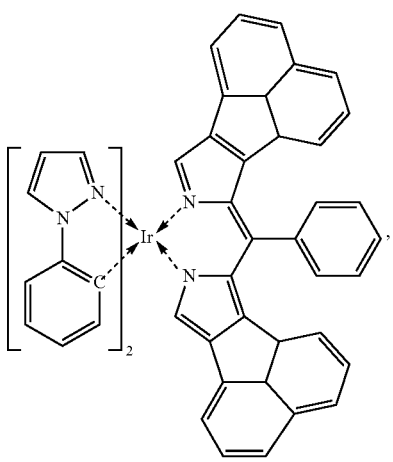

Example M

The DFT calculations for Examples J-O are shown in Table 2 below. These results demonstrate that Examples J-O may have room temperature phosphorescent emissions in the near-IR range. It is believed that the spectral characteristics predicted by DFT calculations will be identical or substantially similar to those that could be obtained by experimental measurement. Thus, Examples J-O may be useful as near-IR phosphorescent emitting compounds.

TABLE 2

DFT Calculations for Examples J-O.

| Compound Example | HOMO | LUMO | HSOMO | [a]Singlet gap | [b]Triplet gap | [c]Triplet gap (nm) |
|---|---|---|---|---|---|---|
| J | −4.374 | −1.639 | −2.816 | 2.735 | 1.558 | 796 |
| K | −4.868 | −2.391 | −3.374 | 2.477 | 1.494 | 830 |
| L | −4.085 | −1.694 | −2.741 | 2.391 | 1.344 | 923 |
| M | −4.807 | −2.341 | −3.23 | 2.466 | 1.577 | 786 |
| N | −5.103 | −2.147 | −3.579 | 2.956 | 1.524 | 814 |
| O | −4.48 | −1.99 | −3.23 | 2.49 | 1.25 | 992 |

[a]HOMO-LUMO;
[b]HSOMO-HOMO;
[c](1240/T.G. nm)

Device Examples

Various possible organic light-emitting devices, which are representative embodiments of the present invention, will now be described. It is understood that the specific methods, materials, conditions, process parameters, apparatus and the like do not necessarily limit the scope of the invention.

Organic light-emitting devices were fabricated using compound Examples A and C. The devices were constructed as follows (in sequence) on an ITO substrate: NPD as the hole transporting layer at a thickness of 400 Å; 10% dopant in Alq$_3$ as the emissive layer at a thickness of 300 Å; and BCP as the electron transport layer at a thickness of 400 Å. The cathode consisted of 10 Å of LiF followed by 1,200 Å of Al.

Figure 10:
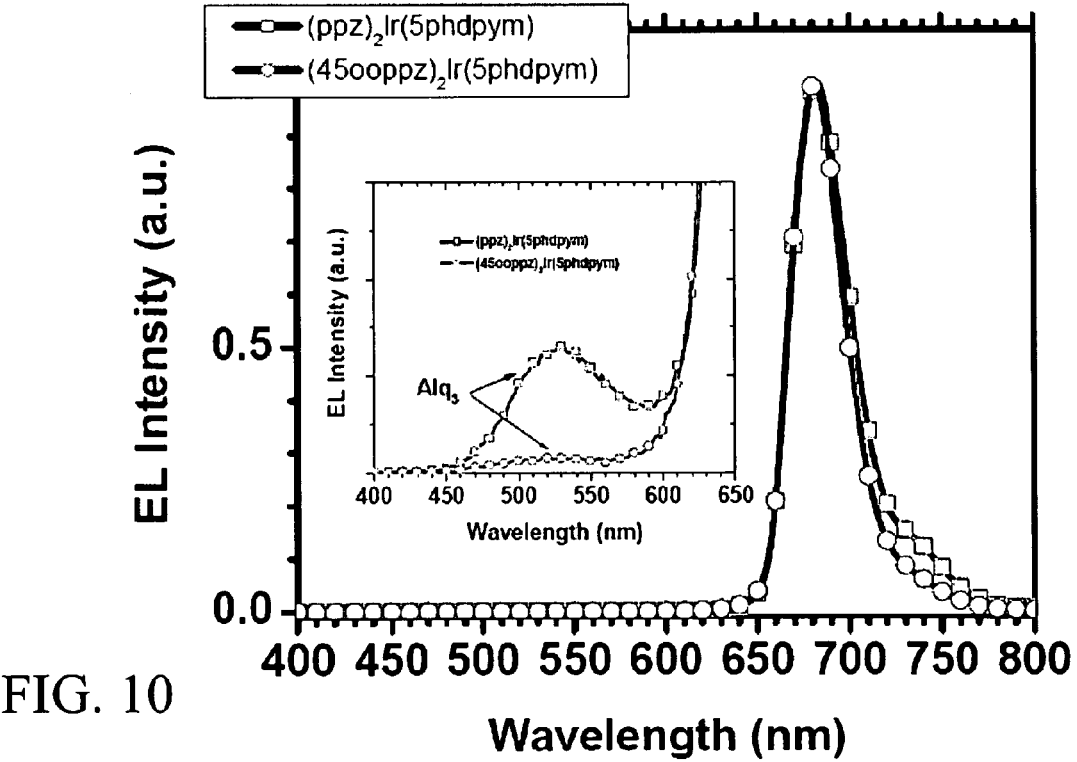
FIG. 10 shows the electroluminescence spectra of device Examples 1 and 2.

Device Example 1 used compound Example A and device Example 2 used compound Example C as the dopant in the emissive layer. The electroluminescent spectra of device Examples 1 and 2 are shown in FIG. 10. The line designated as "(PPz)$_2$Ir(5phdpym)" represents device Example 1 and the line designated as "(45ooppz)$_2$Ir(5phdpym)" represents device Example 2. Both devices produced a phosphorescent emission with λ(max) of 682 nm and a bandwidth of approximately 35 nm (measured full-width at half-maximum). Table 3 below summarizes the characteristics of device Examples 1 and 2.

TABLE 3

Characteristics of Device Examples 1 and 2.

| Device Example | EL λ$_{max}$ nm | CIE Coordinates (x, y) | Turn ON Voltage (@ 1.0 Cd/m$^2$) | Max Brightness (Cd/m$^2$) | Max Device Efficiency (%) |
|---|---|---|---|---|---|
| 1 | 682 | 0.71, 0.29 | 5.9 | 100 | 1.0 |
| 2 | 682 | 0.73, 0.27 | 6.0 | 100 | 0.6 |

The following exemplary metalloporphyrin compound was synthesized:

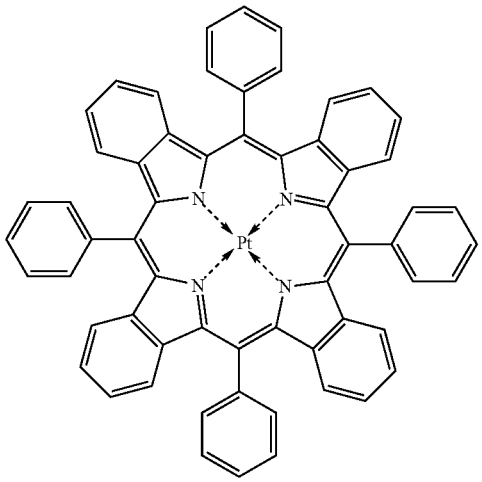

Example P

Tetraphenyl-Pt(II)-tetrabenzoporphyrin

Figure 11:
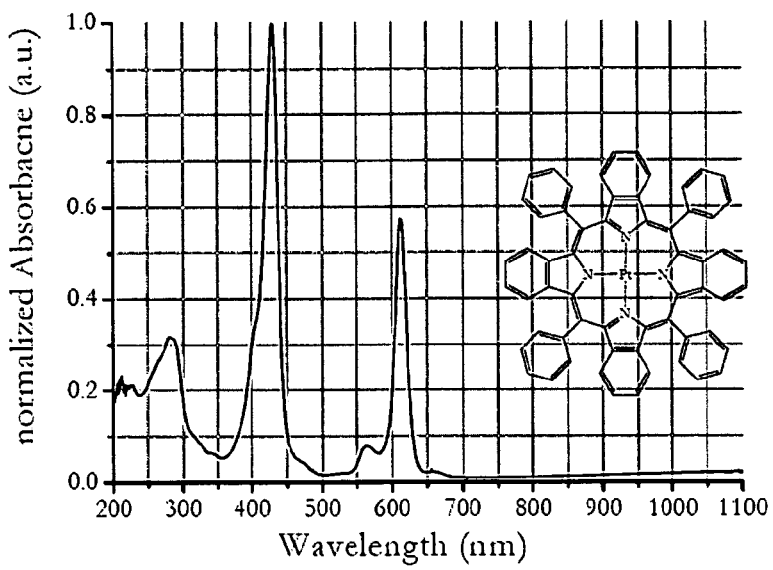
FIG. 11 shows the absorption spectrum of compound Example P in solution.
Figure 12:
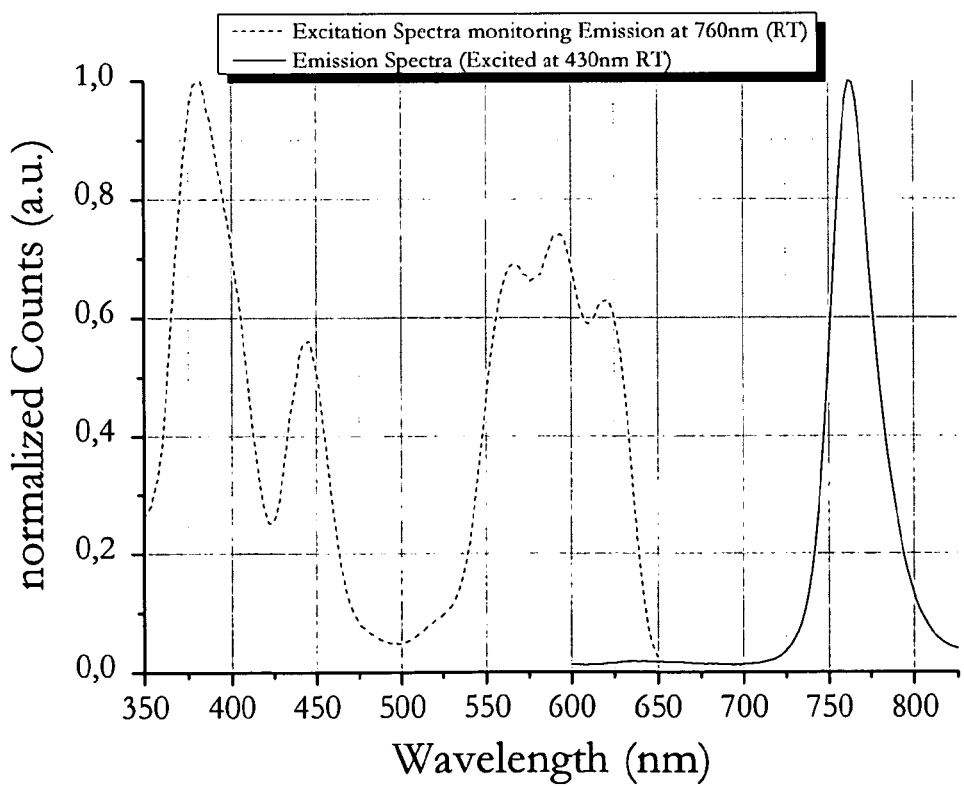
FIG. 12 shows the photoluminescence and excitation spectra of compound Example P in solution.
Figure 13:
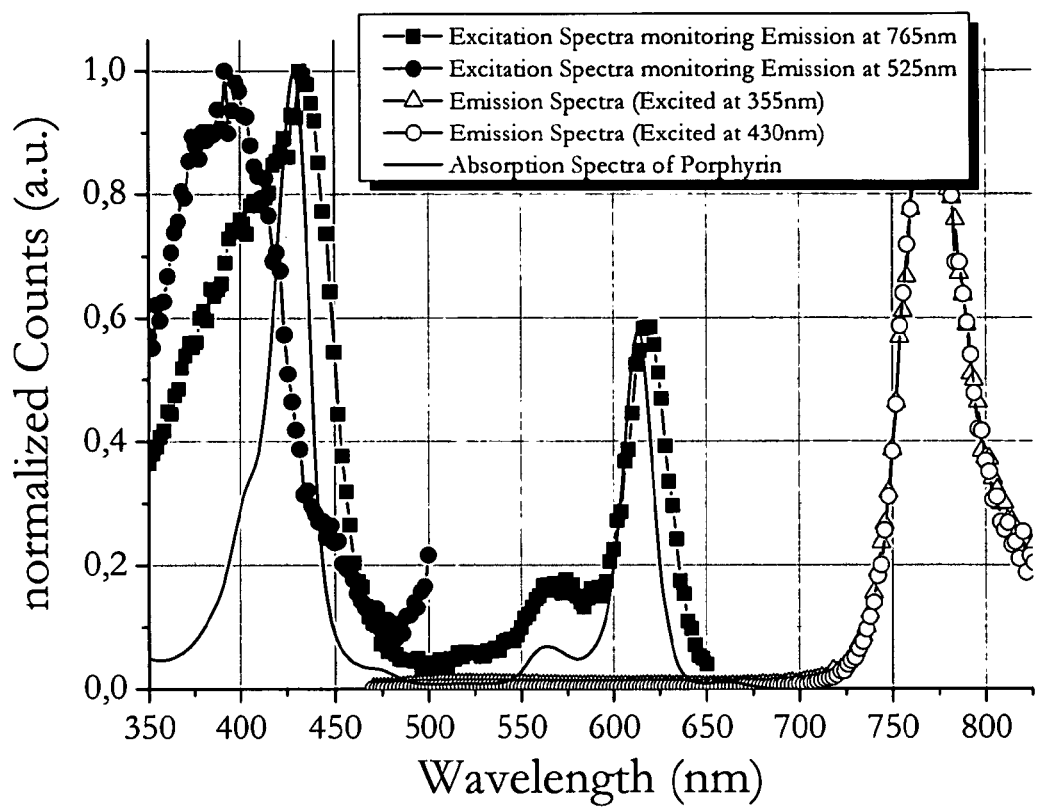
FIG. 13 shows the photoluminescence and excitation spectra of compound Example P in a 5% film.

The various spectral characteristics of compound Example P are shown in FIGS. 11-13. FIG. 11 shows the absorption spectrum of compound Example P by solution spectroscopy in a 2-MeTHF solution. FIG. 12 shows the room temperature photoluminescence and excitation spectra (with emission monitored at 760 nm) of compound Example P by solution spectroscopy in a 2-MeTHF solution. FIG. 13 shows the photoluminescence and excitation spectra (with emission monitored at 765 nm and 525 nm) of a 5% film of compound Example P in an Alq$_3$ host. Host emission (which would be expected at 525 nm) is not detected, indicating that compound Example P may completely quench the Alq$_3$ emission. When used as a dopant in an emissive layer, compound Example P may improve emission efficiency by its host emission quenching effect.

Organic devices were fabricated using compound Example P. The devices were fabricated on a glass substrate precoated with indium tin oxide (ITO) as the anode. The substrates were cleaned with solvent and UV-treated for 10 minutes immediately prior to loading into a high vacuum (~3×10$^{-6}$ Torr) chamber. The organic materials Alq$_3$, NPD, and the metalloporphyrin compounds were purified by sublimation prior to use. Metal cathode materials, Al and LiF (both Aldrich) were used as received. For device Example 3, the layers were deposited by vacuum thermal evaporation as follows (in sequence): A hole transport layer was formed by depositing NPD at 2-2.5 Å/sec to a 400 Å thickness. An emissive layer was formed by co-depositing tetraphenyl-Pt(II)-tetrabenzoporphyrin (dopant) at 0.2 Å/sec followed by Alq$_3$ at 3.8 Å/sec to a 400 Å thickness. An exciton blocking layer was formed by depositing Alq$_3$ at 2-2.5 Å/sec to a thickness of 400 Å. A cathode layer was formed by depositing LiF at 0.2 Å/sec to 10 Å thickness, followed by Al at 3.5-4 Å/sec to a 1100 Å thickness. The cathode layer was evaporated through a mask with a 2 mm slit making the total device area 4 mm$^2$.

Device Example 4 was constructed in the same fashion as device Example 3, except that the blocking layer was absent. Device Example 5 was constructed in the same fashion as device Example 3, except that BCP was used instead of Alq$_3$ in the blocking layer. The construction of devices Examples 3, 4, and 5 is summarized in Table 4.

TABLE 4

Construction of Device Examples 3, 4, and 5.

| Device Example | HTL | EML host | EML dopant | Blocking Layer |
|---|---|---|---|---|
| 3 | NPD | Alq$_3$ | 6% Example P | Alq$_3$ |
| 4 | NPD | Alq$_3$ | 6% Example P | none |
| 5 | NPD | Alq$_3$ | 4% Example P | BCP |

Figure 14:
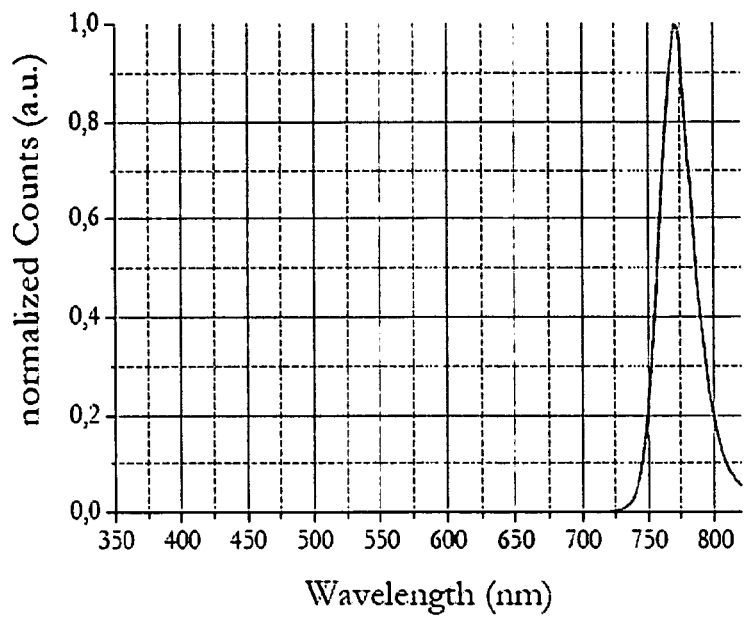
FIG. 14 shows the electroluminescence spectrum produced by device Example 3.
Figure 15:
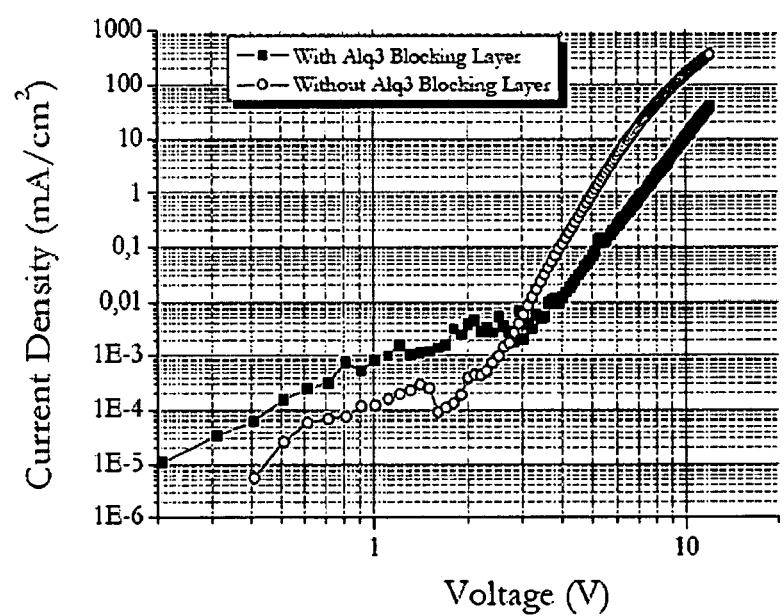
FIG. 15 shows a voltage v. current density plot of device Examples 3 and 4.
Figure 16:
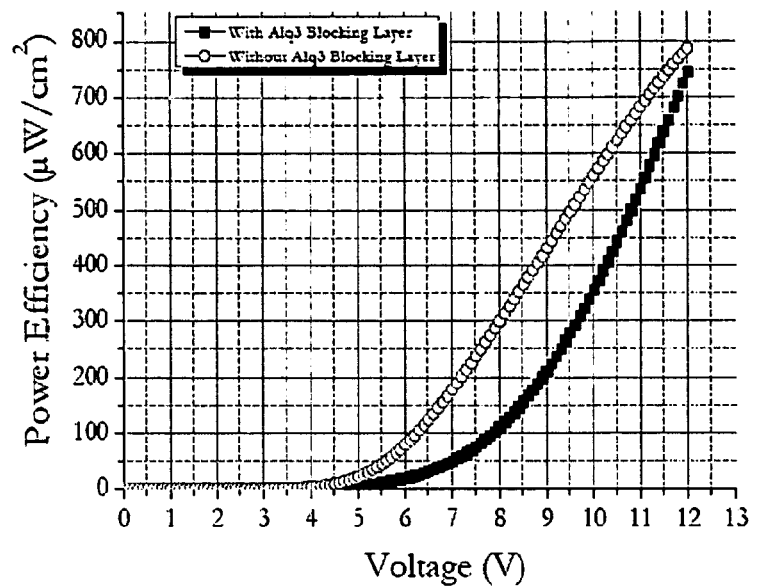
FIG. 16 shows a voltage v. power efficiency plot of device Examples 3 and 4.
Figure 17:
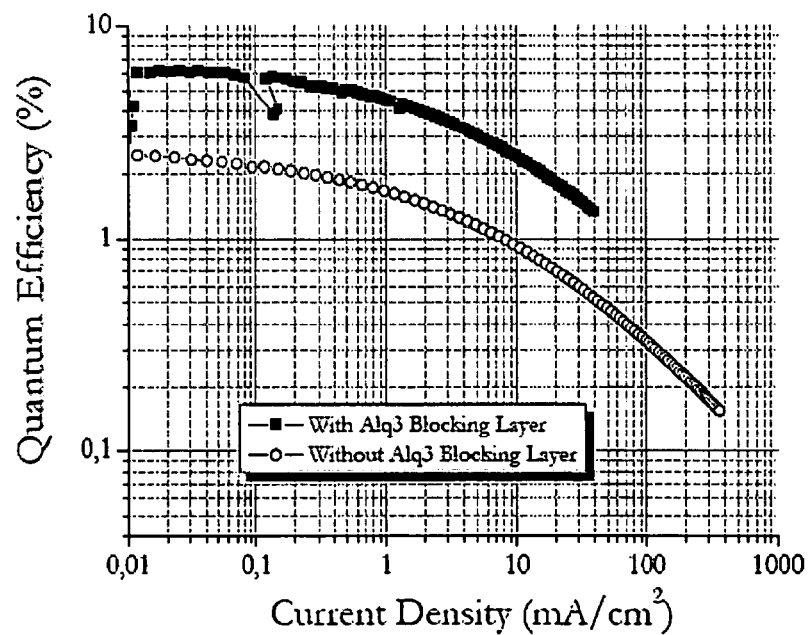
FIG. 17 shows a current density v. quantum efficiency plot of device Examples 3 and 4.
Figure 18:
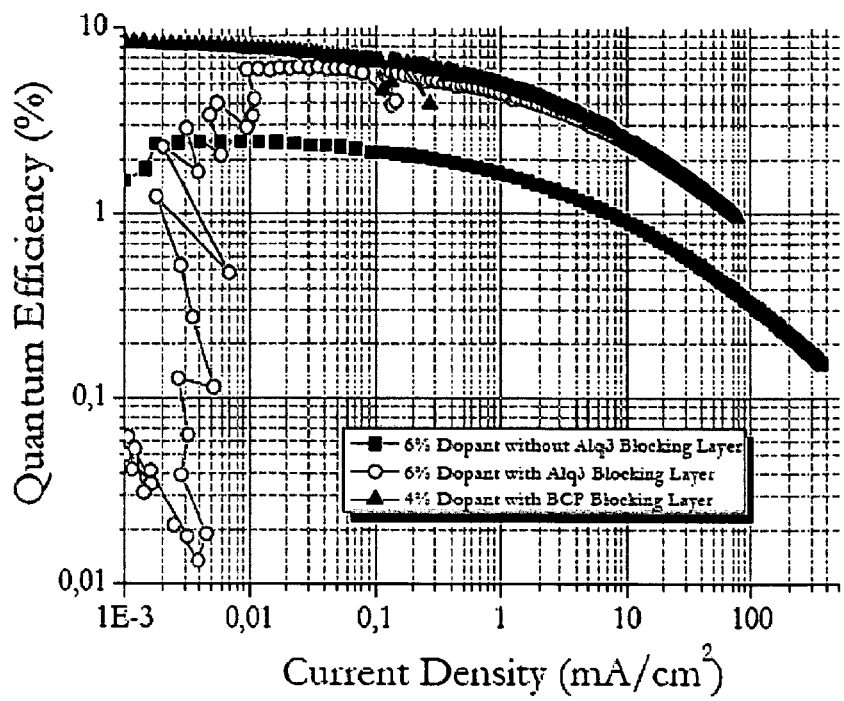
FIG. 18 shows a current density v. quantum efficiency plot of device Examples 3, 4, and 5.
Figure 19:
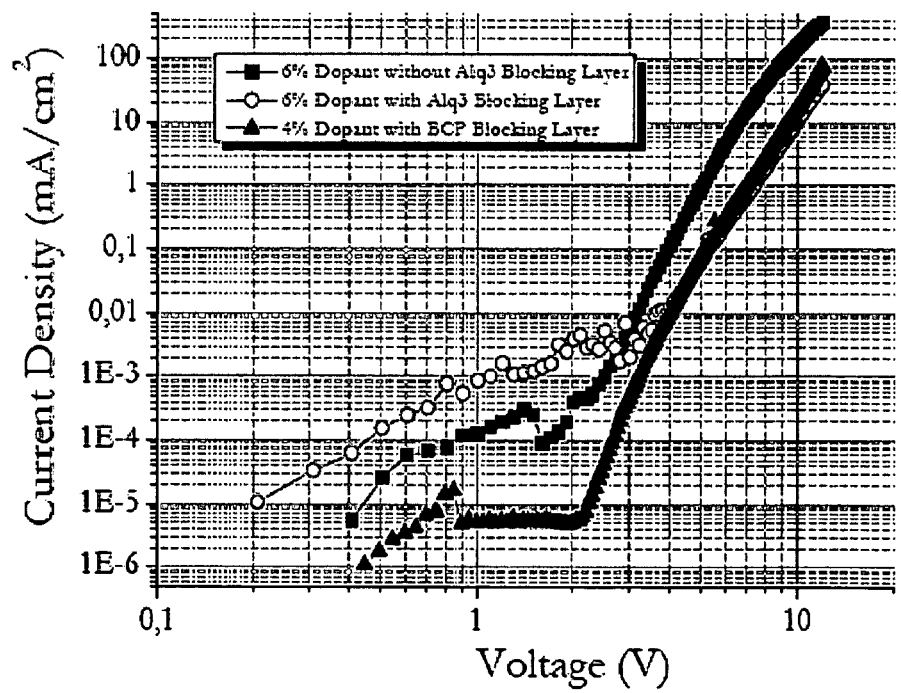
FIG. 19 shows a voltage v. current density plot of device Examples 3, 4, and 5.

The electrical and electroluminescent characteristics of the devices were measured with a Keithly 2400 source/meter/2000 multimeter coupled to a Newport 1835-C optical meter equipped with a UV-818 Si photodetector. FIG. 14 shows the electroluminescence spectrum produced by device Example 3 at 5V. FIGS. 15-19 show various opto-electrical characteristics of device Examples 3, 4, and 5. These results demonstrate that the use of an exciton blocking layer results in higher external quantum efficiencies (EQE, measured at 10$^{-2}$ mA/cm$^2$) of 6% (for device Example 3) or 8.5% (for device Example 5) as compared to the 2% obtained by device Example 4 without a blocking layer. Without intending to be bound by theory, it is believed that the exciton blocking layer between the emissive layer and the metal cathode may serve to decrease the amount of exciton quenching at the metal interface.

It is understood that the various embodiments described herein are by way of example only, and are not intended to limit the scope of the invention. For example, many of the materials and structures described herein may be substituted with other materials and structures without deviating from the spirit of the invention. It is understood that various theories as to why the invention works are not intended to be limiting. For example, theories relating to charge transfer are not intended to be limiting.

MATERIAL DEFINITIONS

As used herein, abbreviations refer to materials as follows:
CBP: 4,4'-N,N-dicarbazole-biphenyl
m-MTDATA 4,4',4"-tris(3-methylphenylphenlyamino)triphenylamine
Alq$_3$: 8-tris-hydroxyquinoline aluminum
Bphen: 4,7-diphenyl-1,10-phenanthroline
n-BPhen: n-doped BPhen (doped with lithium)
F$_4$-TCNO: tetrafluoro-tetracyano-quinodimethane
p-MTDATA: p-doped m-MTDATA (doped with F$_4$-TCNQ)
Ir(ppy)$_3$: tris(2-phenylpyridine)-iridium
Ir(Ppz)$_3$: tris(1-phenylpyrazoloto,N,C(2')iridium(III)
BCP: 2,9-dimethyl-4,7-diphenyl-1,10-phenanthroline
TAZ: 3-phenyl-4-(1'-naphthyl)-5-phenyl-1,2,4-triazole
CuPc: copper phthalocyanine.
ITO: indium tin oxide
NPD: N,N'-diphenyl-N—N'-di(1-naphthyl)-benzidine
TPD: N,N'-diphenyl-N—N'-di(3-toly)-benzidine
BAlq: aluminum(III)bis(2-methyl-8-hydroxyquinolinato)4-phenylphenolate
mCP: 1,3-N,N-dicarbazole-benzene
DCM: 4-(dicyanoethylene)-6-(4-dimethylaminostyryl-2-methyl)-4H-pyran
DMQA: N,N'-dimethylquinacridone
PEDOT:PSS: an aqueous dispersion of poly(3,4-ethylene-dioxythiophene) with polystyrenesulfonate (PSS)

What is claimed is:

1. An organic light-emitting device comprising:
   an anode;
   a cathode; and
   an organic layer between the anode and the cathode, the organic layer comprising a host material and a metalloporphyrin compound, wherein the metalloporphyrin compound comprises a plurality of pyrrole rings and has a formula:

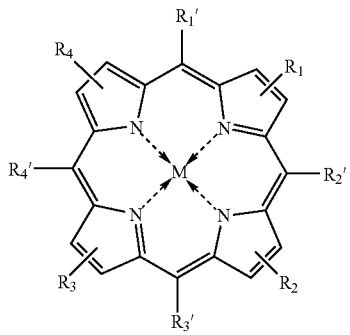

wherein M is a metal;
   wherein each of R$_1$ to R$_4$ is independently selected from the group consisting of an aliphatic moiety, aryl moiety, heteroaryl moiety, and macrocycle moiety;
   wherein each of R$_1$' to R$_4$' is independently selected from the group consisting of a hydrogen, phenyl, mesityl, and methyl;
   wherein the metalloporphyrin compound has a primary phosphorescent photoluminescence emission peak wavelength in the near-infrared range; and
   wherein the absorption spectrum of the metalloporphyrin compound overlaps with the emission spectrum of the host material.

2. The organic device of claim 1, wherein the metalloporphyrin compound has a primary phosphorescent photoluminescence emission peak wavelength greater than about 680 nm.

3. The organic device of claim 1, wherein the metalloporphyrin compound has a primary phosphorescent photoluminescence emission peak with a bandwidth less than about 60 nm.

4. The organic device of claim 1, wherein each of $R_1$ to $R_4$ is an aryl moiety or heteroaryl moiety.

5. The organic device of claim 4, wherein each of $R_1$ to $R_4$ is independently selected from the group consisting of:

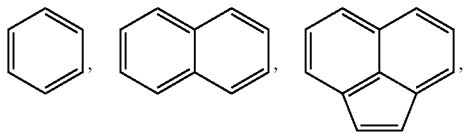

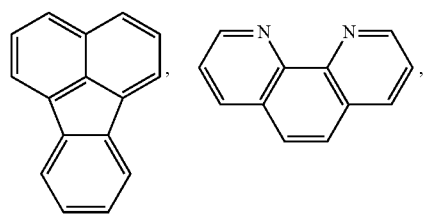

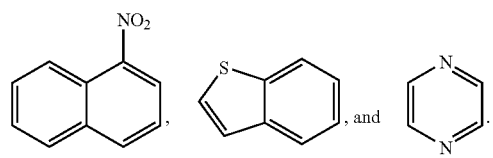

6. The organic device of claim 4, wherein each of $R_1$ to $R_4$ is fused to the adjoining pyrrole ring.

7. The organic device of claim 1, wherein M is platinum.

8. The organic device of claim 1, wherein each of $R_1'$ to $R_4'$ is a phenyl.

9. The organic device of claim 1, wherein the metalloporphyrin compound has the formula:

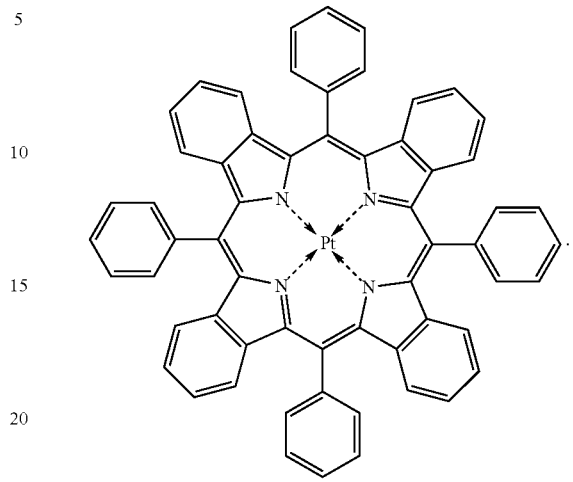

10. The organic device of claim 1, wherein the organic layer is an emissive layer.

11. The organic device of claim 9, wherein the organic layer is an emissive layer.

12. The organic device of claim 4, wherein the organic layer is an emissive layer.

13. The organic device of claim 5, wherein the organic layer is an emissive layer.

14. The organic device of claim 6, wherein the organic layer is an emissive layer.

15. The organic device of claim 1, wherein each of $R_1$ to $R_4$ is an aryl or heteroaryl moiety that is fused to the adjoining pyrrole ring, wherein each of $R_1'$ to $R_4'$ is a phenyl, wherein M is platinum, and wherein the organic layer is an emissive layer.

16. The organic device of claim 5, wherein M is platinum.

17. The organic device of claim 4, wherein each of $R_1$ to $R_4$ is fused to the adjoining pyrrole ring, wherein each of $R_1'$ to $R_4'$ is a phenyl, and wherein M is platinum.

* * * * *